United States Patent
Kondoh et al.

(10) Patent No.: US 8,137,372 B2
(45) Date of Patent: Mar. 20, 2012

(54) TISSUE SHREDDING DEVICE AND TISSUE SHREDDING METHOD

(75) Inventors: Nobuko Kondoh, Hachioji (JP); Kiyotaka Matsuno, Sagamihara (JP)

(73) Assignee: Olympus Medical Systems Corp., Tokyo (JP)

(*) Notice: Subject to any disclaimer, the term of this patent is extended or adjusted under 35 U.S.C. 154(b) by 807 days.

(21) Appl. No.: 11/714,340

(22) Filed: Mar. 6, 2007

(65) Prior Publication Data
US 2008/0221604 A1   Sep. 11, 2008

(51) Int. Cl.
*A61B 17/32* (2006.01)
(52) U.S. Cl. ........................................ 606/170
(58) Field of Classification Search ............ 600/37; 606/45–47, 106, 110, 113–114, 127
See application file for complete search history.

(56) References Cited

U.S. PATENT DOCUMENTS
5,443,472 A * 8/1995 Li .................. 606/114
5,611,803 A   3/1997 Heaven et al.
5,735,289 A   4/1998 Pfeffer et al.

FOREIGN PATENT DOCUMENTS
EP   1 815 811 A2   8/2007

OTHER PUBLICATIONS
U.S. Appl. No. 11/346,711, filed Feb. 3, 2006, Minosawa et al.

* cited by examiner

*Primary Examiner* — S. Thomas Hughes
*Assistant Examiner* — Ashley Cronin
(74) *Attorney, Agent, or Firm* — Scully, Scott, Murphy & Presser, P.C.

(57) ABSTRACT

A tissue shredding device is provided which includes a shredding pipe which is inserted into a patient body in which a plurality of opening portions is formed in a longitudinal direction; and a plurality of wires which is withdrawn from the opening portion, bent back outside the shredding pipe, and drawn into the shredding pipe. Here, the tissue shredding device may be changed to one of a first arrangement in which the wires are withdrawn from the shredding pipe so that a tissue can be introduced toward top portions corresponding to bent-back parts of the plurality of wires, a second arrangement in which the top portions are arranged opposite to the shredding pipe, and a third arrangement in which the wires are drawn into the opening portion.

20 Claims, 30 Drawing Sheets

TISSUE SHREDDING DEVICE AND TISSUE SHREDDING METHOD

BACKGROUND OF THE INVITATION

1. Field of the Invention

The present invention relates to a device and a method for shredding a tissue of a patient's body.

2. Background Art

A medical practice performed on human tissues includes laparoscopic surgery manually performed by opening a plurality of openings on an abdominal wall instead of incising an abdominal wall deeply, and inserting a hard treatment instrument such as an abdominoscope or forceps into each of the openings one by one. In the laparoscopic surgery, since small openings are only just opened, the laparoscopic surgery has advantages of being less invasive and allowing quick recovery of a patient.

The abdominal wall may be incised to a size in which the human tissues can be withdrawn at the time of extirpating human tissues such as a kidney and the like in the laparoscopic surgery, but it is not necessary to incise the abdominal wall deeply at the time of withdrawing the shredded human tissues after finely shredding the human tissues to a predetermined size in an abdominal cavity. An instrument used for this medical procedure includes an instrument in which a cylindrical-shaped head body is inserted into a body cavity and a filamentous body extends to two rows of insertion holes provided in the head body. The filamentous body passes through the head body, is withdrawn from a first insertion hole to the outside of the head body, and is drawn into a second insertion hole in a loop. A loop part of the filamentous body serves as a loop-shaped cutter part cutting the human tissues. Both ends of the filamentous body are fixed in an operating member. The human tissues pass through an inside of the loop-shaped cutter part and the operating member is pulled in an axial direction of the instrument at the time of cutting the human tissues. The loop-shaped cutter part is drawn into the head body from two insertion holes and a loop diameter of the loop-shaped cutter part decreases, whereby the human tissues are cut.

SUMMARY OF THE INVITATION

According to a first aspect of the invention, a tissue shredding device includes a shredding pipe which is inserted into a patient's body in which a plurality of opening portions is formed in a longitudinal direction; and a plurality of wires which is withdrawn from the opening portions, bent back outside the shredding pipe, and drawn into the shredding pipe, wherein the tissue shredding device is switched to one of a first arrangement in which the wires are withdrawn from the shredding pipe so that a tissue can be introduced toward top portions corresponding to bent-back parts of the plurality of wires, a second arrangement in which the top portions are arranged opposite to the shredding pipe, and a third arrangement in which the wires are drawn into the opening portions.

According to a second aspect of the invention, a tissue shredding method using a tissue shredding device having a shredding pipe inserted into a patient's body and wires withdrawn from a plurality of opening portions formed in a longitudinal direction of the shredding pipe one by one, bent-back outside the shredding pipe, and drawn into the shredding pipe from the same opening portion includes the steps of withdrawing the wires from the shredding pipe so as to receive a tissue toward top portions corresponding to bent-back parts of the plurality of wires; arranging the top portions in opposition to the shredding pipe by pulling the wires after introducing the tissue; and shredding the tissue by drawing the wires into the opening portion.

BEST MODE FOR CARRYING OUT THE INVENTION

Hereinafter, exemplary embodiments will be described. In the embodiments, a human tissue such as a kidney is described as a tissue to be cut. Therefore, in the following description, there is exemplified a shape or a size suitable for extirpative surgery in which the kidney is shredded in an abdominal cavity and withdrawn to the outside of a patient's body.

Figure 1:
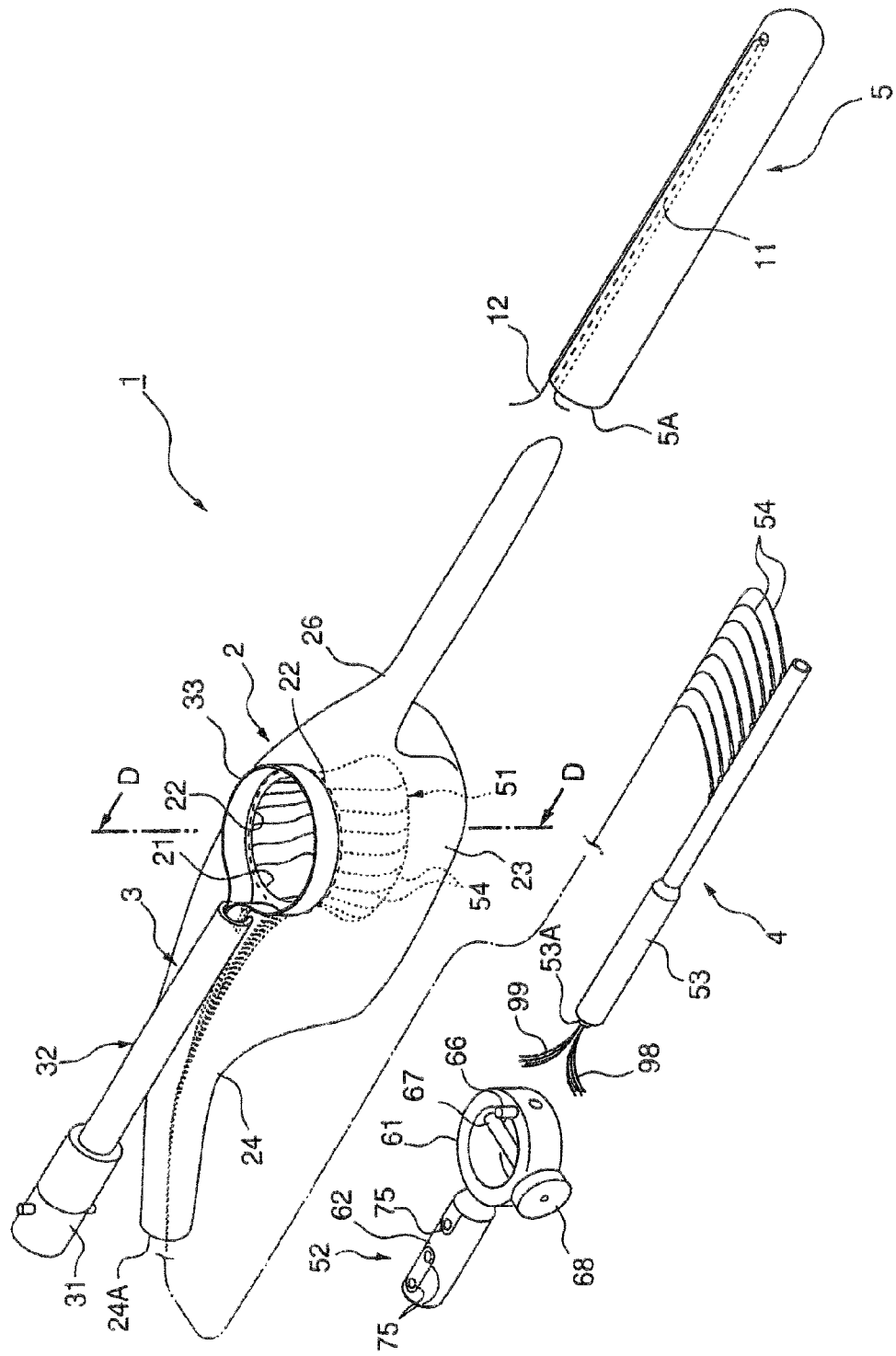
FIG. 1 is a diagram illustrating an entire configuration of a tissue shredding device when a wire of the tissue shredding device is subjected to a first arrangement.

As shown in FIG. 1, a tissue cutting device 1 includes a recovery pouch 2, a tissue recovering unit 3 attached to the outside of the recovery pouch 2 and used with the recovery pouch 2, a shredding device 4 shredding the tissue such as the kidney in the recovery pouch 2, and a cover 5 used at the time of inserting the tissue cutting device 1 into the abdominal cavity.

Figure 2:
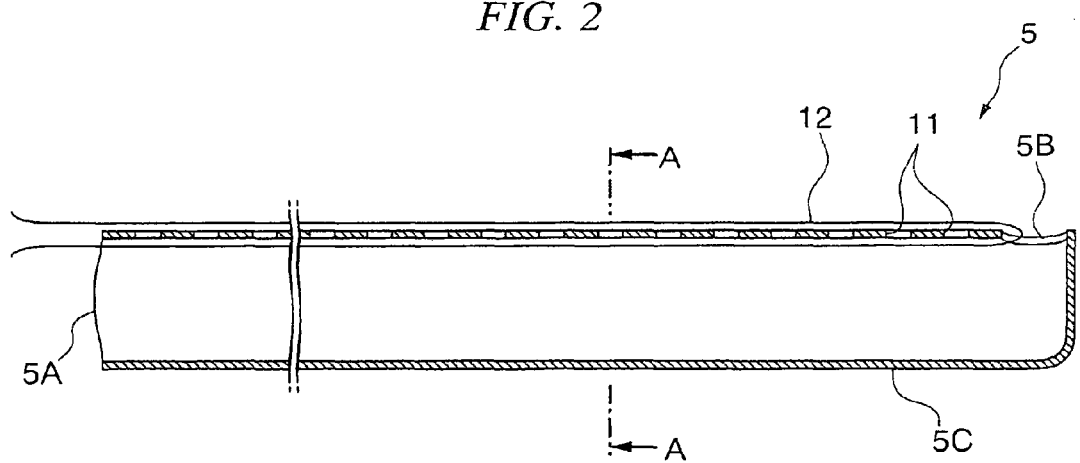
FIG. 2 is a diagram illustrating a cover.
Figure 3:
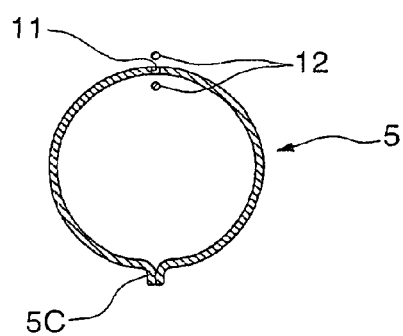
FIG. 3 is a cross-sectional view taken along the line A-A shown in FIG. 2.

As shown in FIGS. 2 and 3, the cover 5 is formed of a pouch body of which a front end inserted into the patient's body is closed and a base end portion in a proximal side is opened. A break section 11 formed of a perforation along a longitudinal direction is provided on a side portion of the cover 5. The break section 11 can be broken with a cover cutting thread 12. The thread 12 is inserted into the cover 5 from an opening 5A provided in the base end side, passes to the front end along the break section 11, and is withdrawn to the outside of the cover 5 from a side hole 5B of the front end. After then, the thread 12 extends to the opening 5A along the break section 11 in the outside of the cover 5. The cover 5 is manufactured by a resin such as polyurethane and an overall length thereof is about 300 mm. A method of manufacturing a pouch-shaped cover by thermally compressing an end portion 5C after forming the break section 11 in a strip-shaped resin material is given as an example of a method of manufacturing the cover 5.

Figure 4:
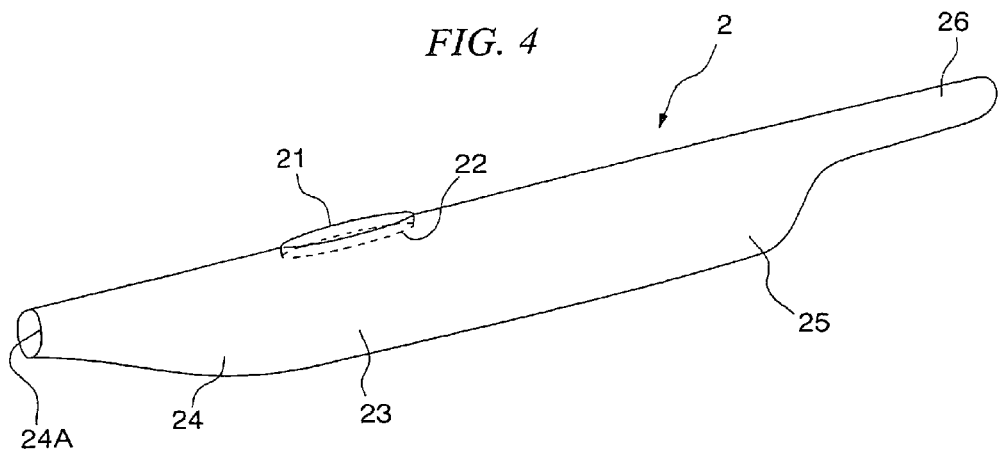
FIG. 4 is an overall view of a recovery pouch.

As shown in FIG. 4, the recovery pouch 2 is formed of an elongated pouch body. One opening portion 21 is formed on a side portion of the recovery pouch 2. A break section 22 formed of the perforation is provided in a peripheral portion of the opening portion 21. An area in which the opening portion 21 is formed in the recovery pouch 2 serves as a housing section 23 in which the tissues are inserted and temporarily housed. A base end side relative to the housing section 23 serves as a handle section 24 handled by an operator. In the handle section 24, the opening 24A is formed after a cross-sectional area of the pouch body becomes slowly decreased toward the base end.

In the recovery pouch 2, a front end side relative to the housing section 23 serves as a shredding cover section 25 allowing the tissues to be disposed at the time of shedding the tissues. The shredding cover section 25 is formed in succession from the housing section 23 and has substantially the same cross-sectional area as the housing section 23, but an opening is not provided in the shredding cover section 25. By this configuration, shredded tissues cannot be disseminated in the body. An extirpation section 26 capable of housing the shredded tissues is formed in front of the shredding cover section 25. The extirpation section 26 has a cross-sectional area smaller than the shredding cover section 25 and has an elongated shape. An opening is also not provided in the extirpation section 26.

The recovery pouch 2 is integrally manufactured by using a material which has flexibility and can observe an inside of the recovery pouch 2 with an abdominoscope. Regarding the size of each of the sections in a longitudinal direction, for example, the sizes in the longitudinal direction of the handle section 24, the housing section 23, the shredding cover section 25, and the extirpation section 26 are set to approximately 200 mm, 170 mm, 300 mm, and 200 mm, respectively. A diameter of the extirpation section 26 is set to approximately 60 mm.

Figure 5:
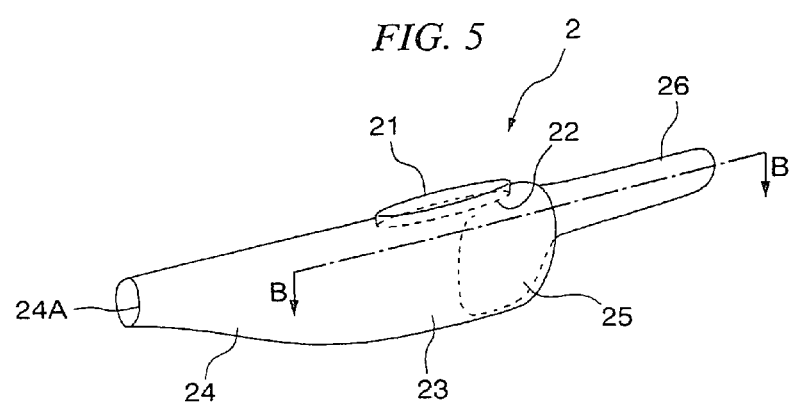
FIG. 5 is a diagram illustrating a state in which a recovery pouch is folded.
Figure 6:
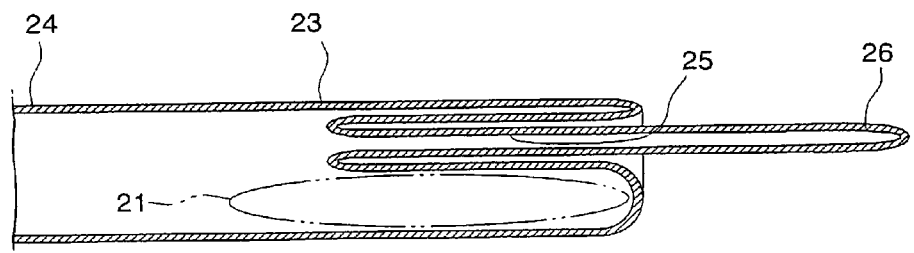
FIG. 6 is a cross-sectional view taken along the line B-B shown in FIG. 5.

As shown in FIGS. 5 and 6, the shredding cover section 25 is folded into the inside of the housing section 23 and is shortened to approximately half, whereby the recovery pouch 2 is inserted into the patient's body. The recovery pouch 2 is wound around a longitudinal axial circumference and is inserted into the cover 5.

Figure 7:
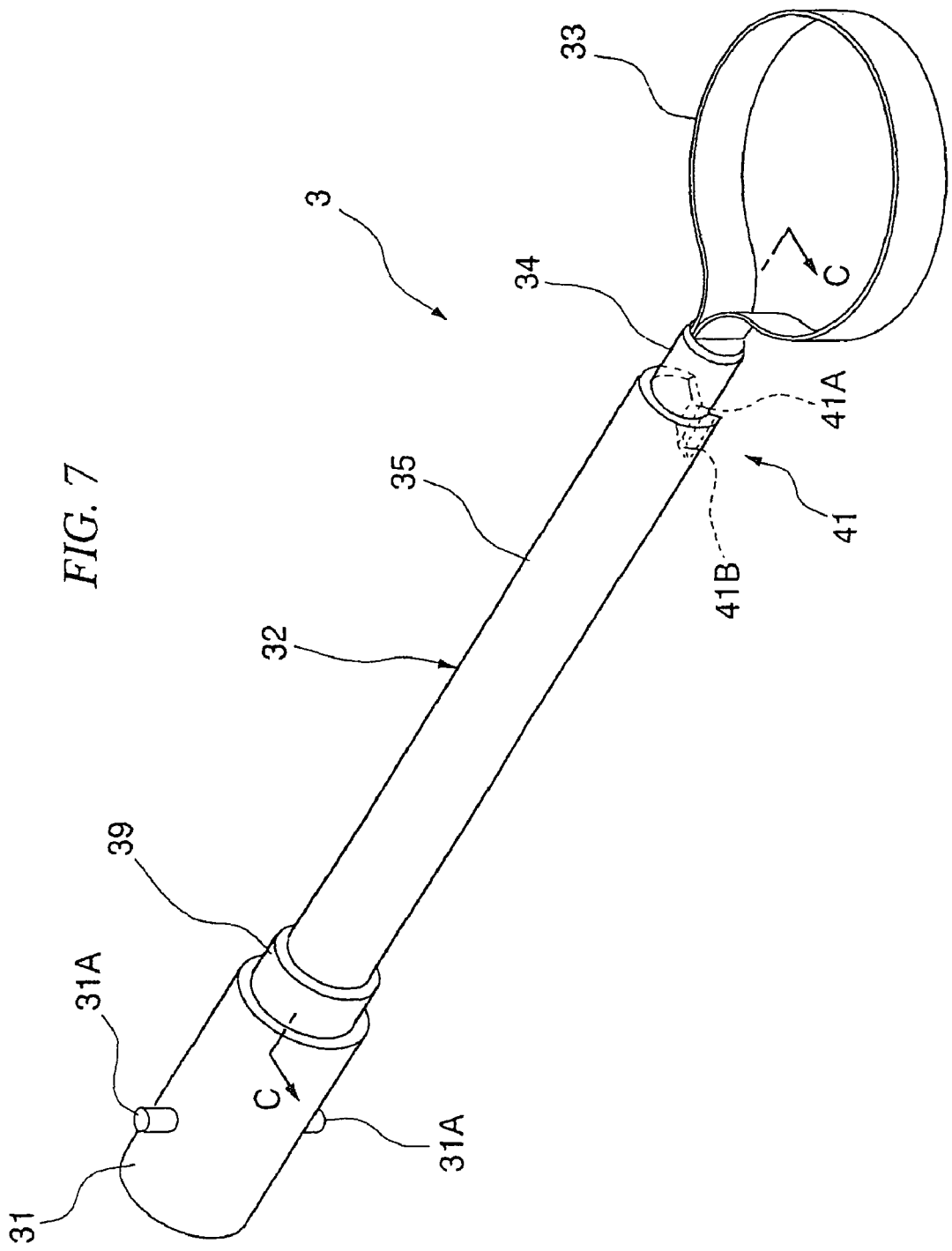
FIG. 7 is a diagram illustrating a tissue recovering unit.

As shown in FIG. 7, the tissue recovering unit 3 has a holding section 31 grasped by the operator and a thin insertion section 32 extends from the holding section 31. A loop-shaped opening support section 33 formed of a strip-shaped member is attached to a front end of the insertion section 32. In the holding section 31, a protrusion portion 31A is provided so that the tissue recovering unit 3 can easily rotate on an axial line.

The insertion section 32 has a pipe 34 fixed in the holding section 31 and a pouch cutting pipe 35 provided in the outside of the pipe 34 so as to advance and retreat. A solid rod may be used instead of the pipe 34.

Figure 8:
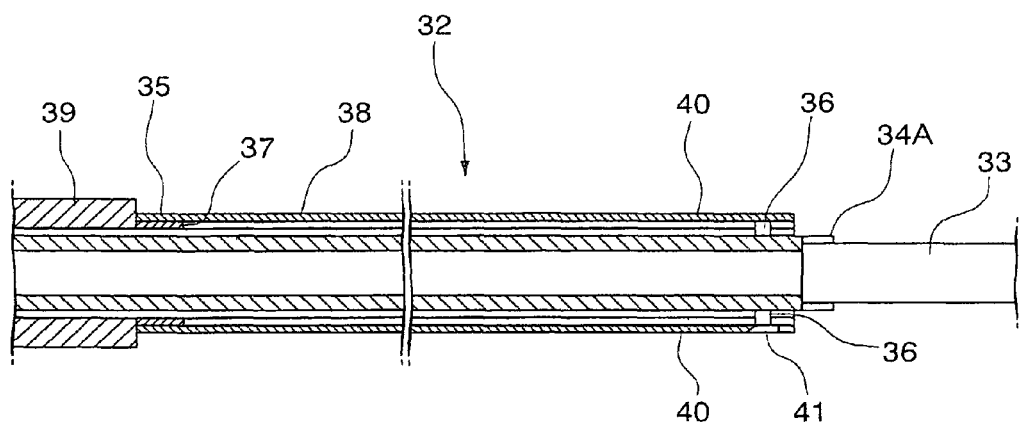
FIG. 8 is a cross-sectional view taken along the line C-C shown in FIG. 7.

As shown in FIG. 8, a slot 34A is provided in a front end of the pipe 34 and the opening support section 33 is inserted into the slot 34A and fixed by soldering. Protrusions 36 protruding in a diameter direction are provided in the front end of the pipe 34. The pouch cutting pipe 35 has a double-tube structure in which an outer pipe 38 is mounted on an inner pipe 37 and a handle 39 having a large diameter is formed in a base end portion thereof. A pair of slits 40 is formed in the inner pipe 37 in a longitudinal direction from a front end of the inner pipe 37. The protrusions 36 of the pipe 34 are inserted into the slits 40 one by one. As a result, the pouch cutting pipe 35 can advance and retreat on the protrusions 36 and rotation thereof is prevented. The slits 40 are terminated in front of a base end of the inner pipe 37 and serve as a stopper preventing the pouch cutting pipe 35 from being removed from the pipe 34.

As shown in FIG. 7, a cutting section 41 is formed in a front end of the outer pipe 38. One cutting section 41 is provided substantially in the same plane as positions in which the protrusions 36 are formed and a cutting blade 41B is formed at the end of a base end side of the slit 41A toward a front end. The cutting blade 41B is formed of a surface which is slanted in a direction closing toward an inner circumferential side from an outer circumferential side. The cutting blade 41B may be formed of a surface which is slanted in a direction opposite to the above-mentioned direction, that is, a surface which is slanted in a direction opening toward the front end. The front end of the slit 41A is expanded so that a circumferential opening is opened.

Figure 9:
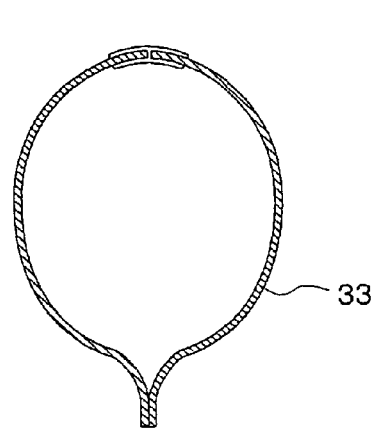
FIG. 9 is a plan view of an opening support section.
Figure 10:
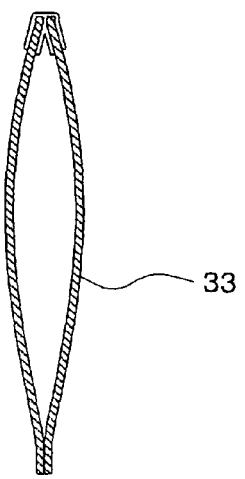
FIG. 10 is a plan view illustrating a state in which the opening support section shown in FIG. 9 is closed.

As shown in FIG. 9, the opening support section 33 is urged by widening a resilient plate, the front end is connected with a thermal contraction tape or a thermal contraction tube, and the opening support section 33 can be opened and closed with a connection part as a central axis. The opening support section 33 has a shape similar to a rugby ball having a short axis of about 90 mm and a long axis of about 140 mm under a no-load condition. The long axis is set to an insertion direction, that is, a longitudinal direction of the insertion section 32. When an external force is applied by pressing a short axis direction, the opening support section 33 is closed as shown in FIG. 10.

Figure 11:
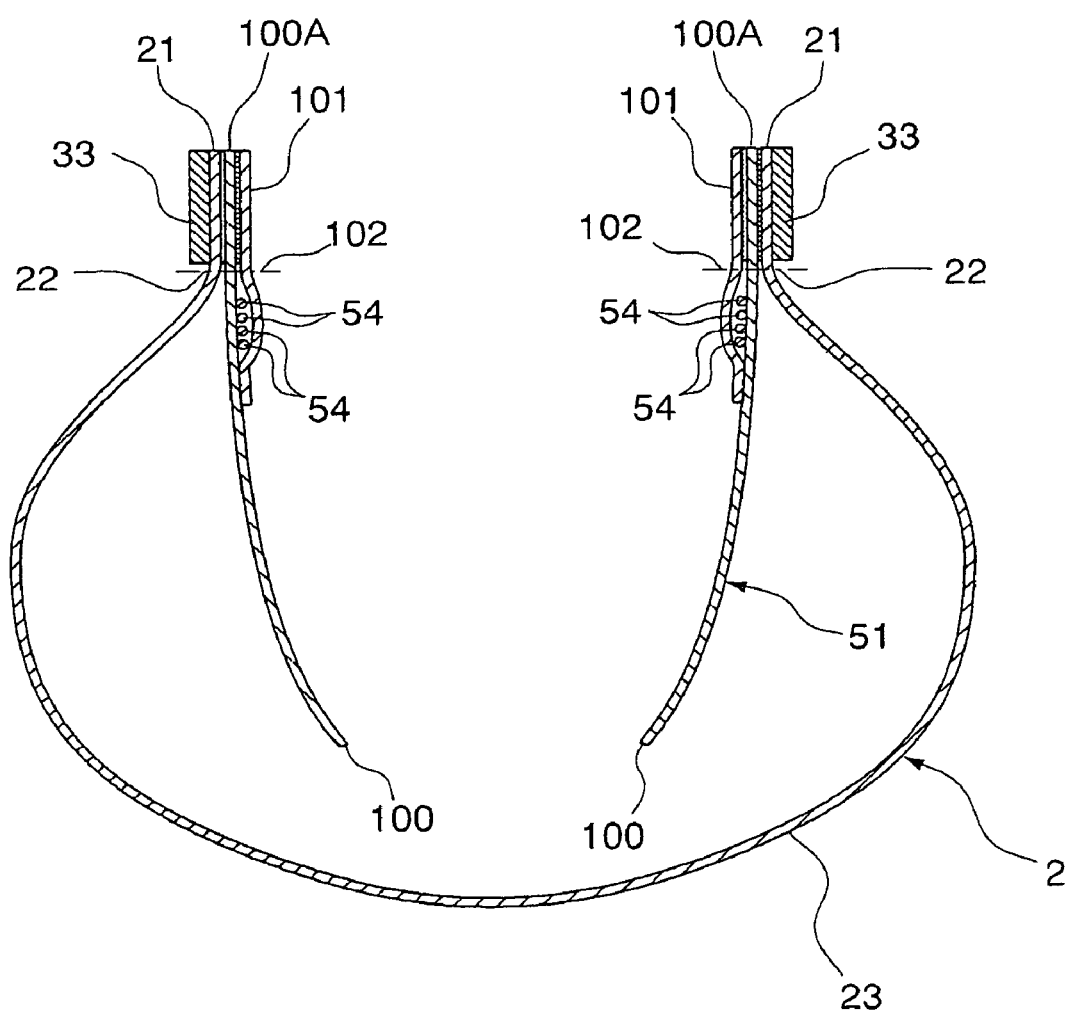
FIG. 11 is a cross-sectional view taken along the line D-D shown in FIG. 1.

As shown in FIGS. 1 and 11, a peripheral portion of the opening portion 21 of the recovery pouch 2 is fixed on an inner circumferential surface of the opening support section 33 by an adhesive agent and the like. An adhesion part is positioned in the opening portion 21 side than the break section 22. As a result, the opening support section 33 has substantially the same shape as the opening portion 21 of the recovery pouch 2 and the shape of the opening portion 21 is held in a state where the opening portion 21 is widened and urged by the opening support section 33 attached to the outside of the opening portion 21. A cutting pouch 51 of the tissue shredding device 4 is fixed on an inner surface of the peripheral portion of the opening portion 21 of the recovery pouch 2 with the adhesive agent and the like.

As shown in FIG. 1, the tissue shredding device 4 has an operating section 52 and a shredding pipe 53 removably mounted on the operating section 52 and a plurality of wires 54 serving as a tissue cutting member is drawn from the shredding pipe 53. The wires 54 are drawn into the recovery pouch 2 from the opening 24A of the handle 24 and are attached to the cutting pouch 51. The wire 54 may be formed of one wire and may be manufactured by twisted wires. In an initial state, the vicinity of a top portion 54A of the wire 54 and the cutting pouch 51 are inserted into the recovery pouch 2.

Figure 12:
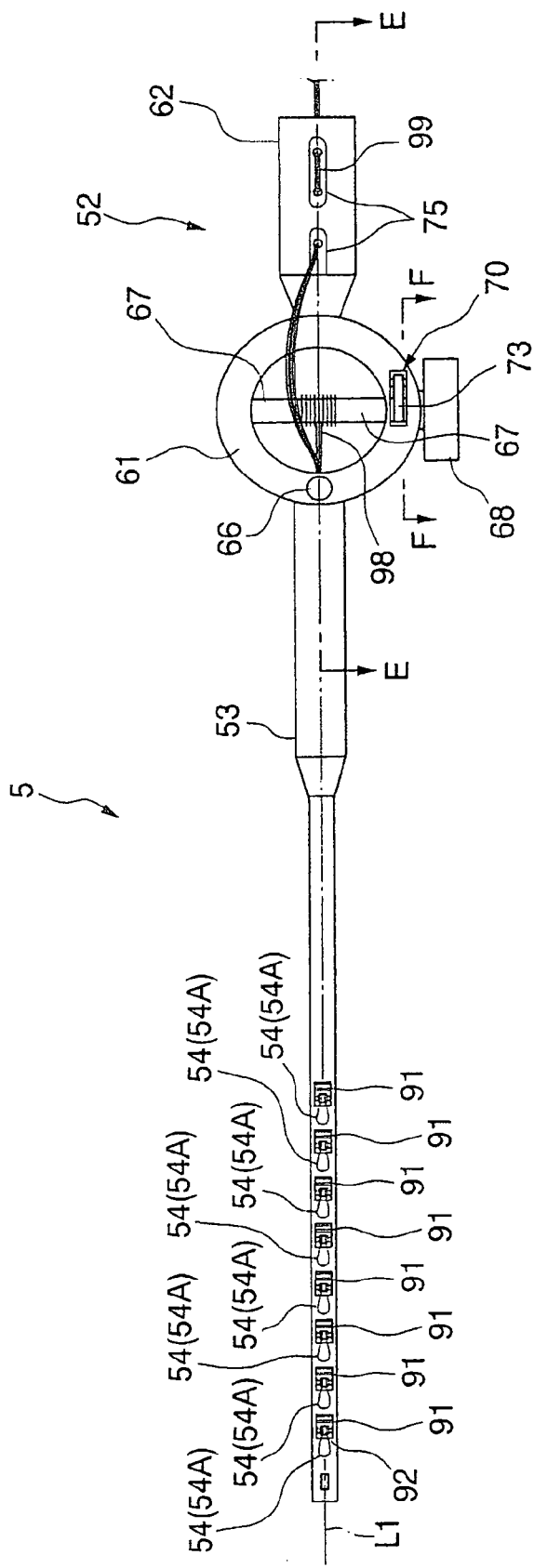
FIG. 12 is a diagram illustrating a tissue shredding device.

FIG. 12 illustrates a state in which the shredding pipe 53 is fixed in the operating section 52. The operating section 52 has a circular operating body 61 and a grip 62 is fixed in a predetermined portion of an outer peripheral surface of the operating body 61.

Figure 13:
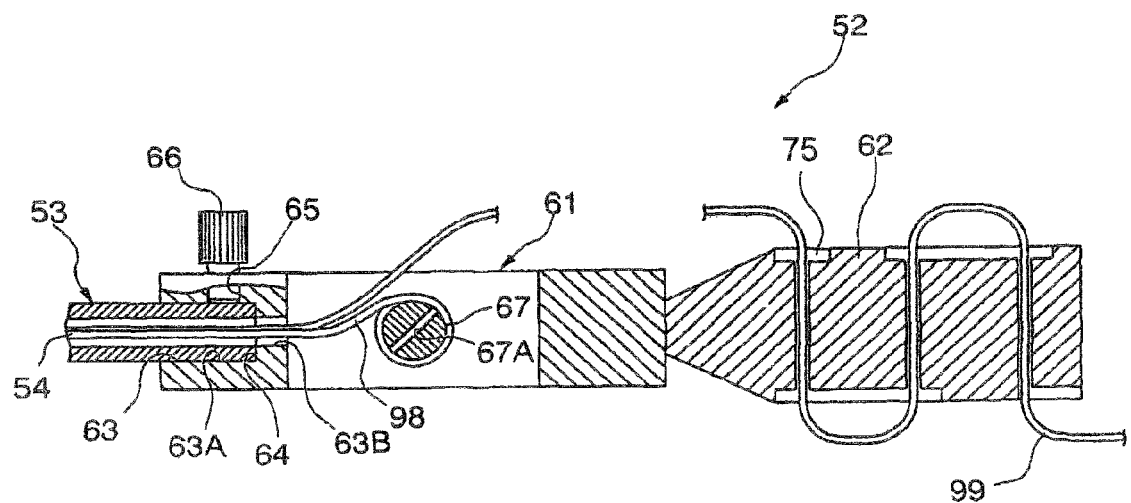
FIG. 13 is a cross-sectional view taken along the line E-E shown in FIG. 12.

The operating body 61 has a ring shape in a plan view and the shredding pipe 53 and the grip 62 are fixed in the operating body 61 so that the shredding pipe 53 and the grip 62 are coaxially disposed. In the shredding pipe 53 side of the opening body 61, a through-hole 63 is bored to penetrate from an outer peripheral surface to an inner peripheral surface. As shown in FIG. 13, in the outer periphery side of the operating body 61, the through-hole 63 has a diameter in which the shredding pipe 53 can be inserted therein. In the through-hole 63, a base end thereof (an inner periphery side of the operating body 61) has a diameter smaller than a front end thereof (an outer periphery side of the operating body 61) and a base end portion of the shredding pipe 53 hits a stepped pulley 64 formed of a large-diameter portion 63A and a small-diameter portion 63B. In the operating body 61, a screw hole 65 which communicates with the large-diameter portion 63A is bored to be orthogonal to an axial line of the through-hole 63. When a screw 66 is screwed into the screw hole 65 and hits the outer periphery of the shredding pipe 53, the shredding pipe 53 can be fixed in the operating body 61.

A shaft 67 serving as an operation member is rotatably supported on the operating body 61 so as to be orthogonal to an axial line connecting the grip 62 and the through-hole 63 (an axial line of the operating section 52). A through-hole 67A is formed on the axial line of the operating section 52 in the shaft 67.

Figure 14:
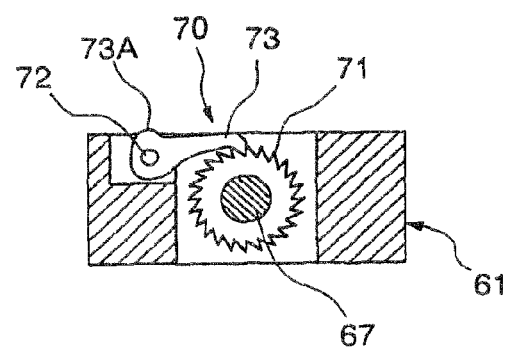
FIG. 14 is a cross-sectional view taken along the line F-F shown in FIG. 12.

As shown in FIG. 12, one end portion of the shaft 67 is withdrawn from the outer peripheral surface of the operating body 61 and a handle 68 is fixed therein. Here, as shown in FIG. 14, a rotation direction of the shaft 67 can be controlled by a ratchet mechanism 70. The ratchet mechanism 70 has a ratchet gear 71 fixed in the shaft 67 and a ratchet claw 73 rotatably supported on the operating body 61 with a pin 72. The ratchet claw 73 urges to engage with the ratchet gear 71 by means of a resilient member not shown. A portion 73A of the ratchet claw 73 is exposed from the operating body 61 to the outside and engagement between the ratchet claw 73 and the ratchet gear 71 can be removed by pressing the portion 73A with a finger.

As shown in FIGS. 12 and 13, a fixation section 75 fixing one end portion of the wires 54 by tying is formed in the grip 62. In the fixation section 75, the grip 62 is counter-bored to fall in one step and a plurality of through-holes is provided to form a crank. In the grip 62, a bundle of the wires 54 are provided by imitating a crank shape of the fixation section 75 and are strongly fixed. Other fixation methods or a fixation method of adding a screw fixation to the crank shape may be used.

As shown in FIG. 1, the shredding pipe 53 has a base end portion having a large diameter and a front end portion having a diameter smaller than the base end portion. In the base end portion, a connection portion 53A inserted into the operating body 61 protrudes.

Figure 15:
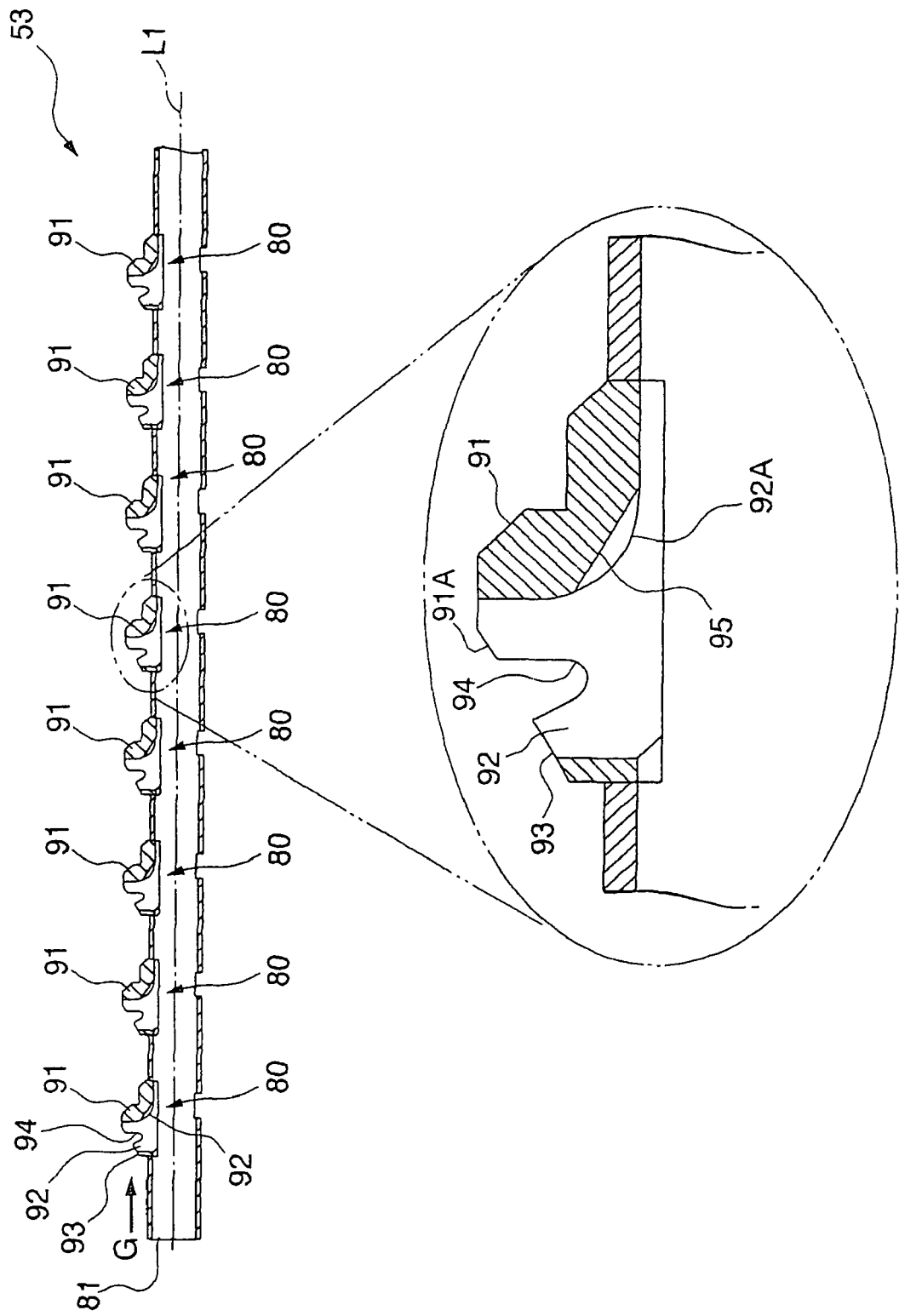
FIG. 15 is a side view of a shredding pipe of a tissue shredding device.

As shown in FIGS. 12 and 15, a plurality of openings 80 are formed in a line on a thin front end portion of the shredding pipe 53 in a longitudinal direction thereof. Each of the openings 80 communicates with a hole 81 penetrating the shredding pipe 53 from the front end to the base end thereof. A direction of each opening 80 is substantially orthogonal to an axial line L1 of the shredding pipe 53. Guide members 91 are fixed in the openings 80, respectively.

Figure 16:
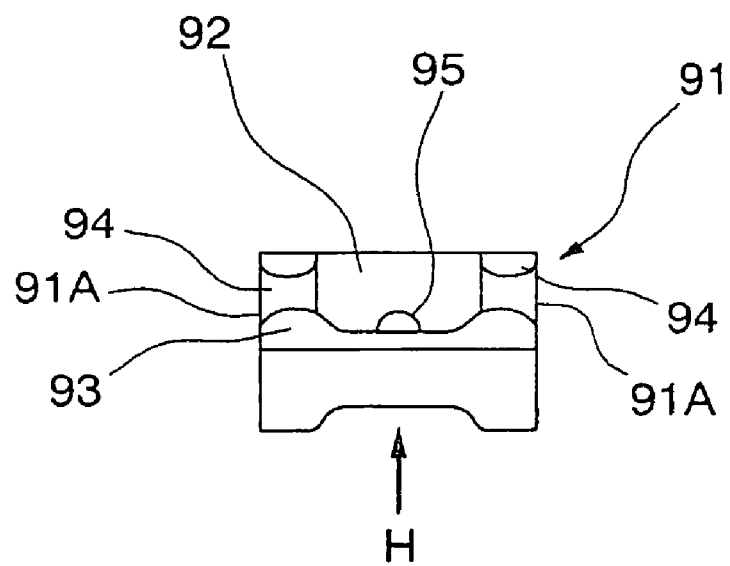
FIG. 16 is a diagram illustrating an external appearance of a guide member attached to a shredding pipe and a diagram viewed from a direction of an arrow G of FIG. 15.

As shown in FIGS. 15 and 16, each of the guide members 91 has an insertion hole 92 which communicates with the hole 81. The insertion hole 92 is opened in a direction substantially orthogonal to the hole 81. The base end side of the axial line L1 side of the insertion hole 92 is extended by a curved surface 92A. The curved surface 92A prevents the wires 54 from being caught. An opening surface 93 of an outer peripheral side of the insertion hole 92 is slanted so that a front end thereof is slanted toward the axial line L1 and an angle between the opening surface 93 and the axial line L1 becomes a sharp angle. Grooves 94 are provided on side wall portions 91A substantially orthogonal to the axial line L1 and a diameter direction, respectively. A part in which the opening surface 93 falls in one step is formed on the side wall portion 91A by the grooves 94. The groove 94 extends toward the axial line L1 from the opening surface 93 and the opening surface 93 side of the groove 94 has a large width. A distal end of the axial line L1 side of the groove 94 is formed of a curved surface having a size in which the wires 54 can be inserted. In the guide member 91, an edge of the opening surface 93 and the groove 94 is chamfered and the wire 54 is difficult to catch.

Figure 17:
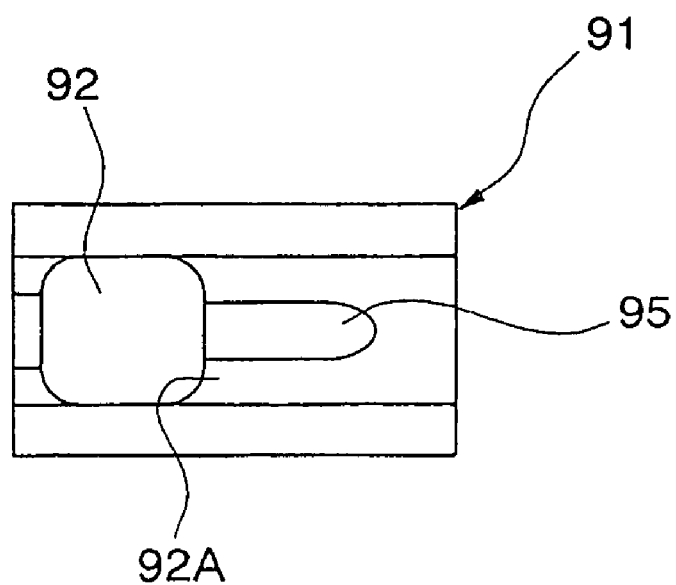
FIG. 17 is a diagram viewed from a direction of an arrow H of FIG. 16.

A guide groove 95 is concaved in a part of the curved surface 92A as shown in FIG. 15 and FIG. 17 in which the guide member 91 is viewed from the axial line L1. The guide groove 95 extends substantially along the axial line L1 and has a width in which only one wire 54 can be inserted. A depth of the guide groove 95 is substantially the same as a diameter of the wire 54. As shown in FIG. 15, an inclination angle of the guide groove 95 is set to a sharp angle to the axial line L1 and an end portion of the opening surface 93 side of the guide groove 95 is provided closer to the outside than to the distal end of the guide groove 95 in a diameter direction.

As shown in FIG. 12, the wire 54 passes through the insertion hole 92 of the guide member 91 and is withdrawn to the outside of the shredding pipe 53. The wire 54 is drawn to the outside of the shredding pipe 53 from one opening 80 and is bent back outside the shredding pipe 53. The wire 54 is drawn into the shredding pipe 53 from the same opening 80 again. Accordingly, a part of the wire 54 drawn to the outside of the shredding pipe 53 is formed substantially in a loop centering on the top portion 54A corresponding to the bent-back portion. The wire 54 passes through the shredding pipe 53 and is drawn into the operating section 52. A first end portion 98 of the wire 54 is fixed in the shaft 67 and a second end portion 99 of the wire 54 is fixed in the grip 62.

The first end portion 98 includes one end portion of the wire 54 passing through odd-numbered openings 80 from the front end side and the other end portion of the wire 54 passing through even-numbered openings 80 out of the wires 54 passing through the shredding pipe 53. The second end portion 99 includes the other end portion of the wire 54 passing through odd-numbered openings 80 from the front end side and one end portion of the wire 54 passing through even-numbered openings 80 out of the wires 54 passing through the shredding pipe 53. In other words, end portions on the same side of two wires 54 disposed adjacent to each other in an axial line direction are attached to different portions of the operating section 52. The first end portion 98 may be fixed in the grip 62 and the second end portion 99 may be fixed in the shaft 67.

Figure 18:
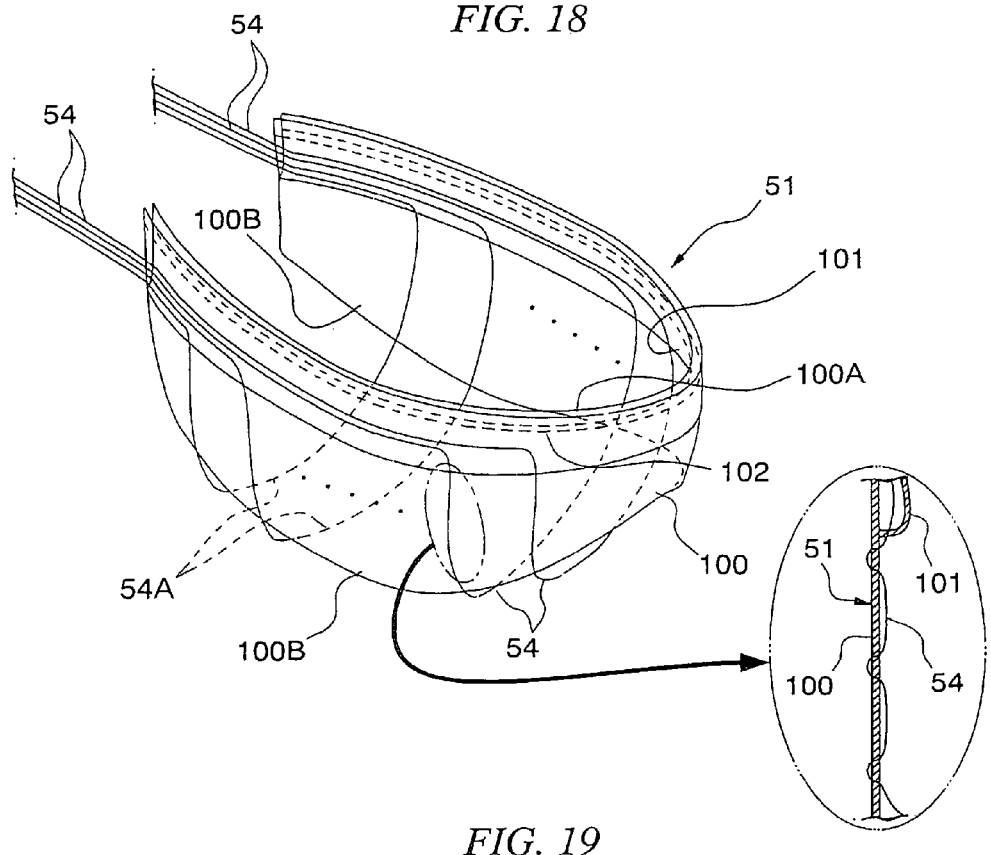
FIG. 18 is a diagram illustrating an external appearance of a cutting pouch and arrangement of wires.

As shown in FIG. 1, a central portion of each of the wires 54 which is bent back in the recovery pouch 2 passes through the cutting pouch 51. As shown in FIGS. 11 and 18, the cutting pouch 51 is formed of a strip-shaped flexible member 100 by benting substantially in a U shape. One edge portion 100A substantially having the U shape has a double structure in which the other strip-shaped member 101 is applied thereto by thermal compression. A break section 102 formed of the perforation is provided in the portion of the double structure. In a pouch-shaped portion by attaching the strip-shaped member 101, a bundle of wires 54 pass through a portion lower than the break section 102. The wires 54 are withdrawn toward the direction substantially orthogonal to the break section 102 at predetermined intervals and alternatively pass through the inside and the outside of the strip-shaped member 100. The wires 54 reach the other edge portions 100B and cross between edge portions 100B. Accordingly, the top portion 54A of the wire 54 has substantially the U shape in a direction substantially orthogonal to a U-shaped geometry of the cutting pouch 51.

The cutting pouch 51 has a size matched with an external diameter of the opening portion 21 and is manufactured of a resin such as polyethylene. A depth in a direction orthogonal to the opening portion 21 is about 100 mm. An arrangement distance and the number of the wires 54 in the strip-shaped member 100 are 15 mm and eight, respectively.

As shown in FIG. 1, in an initial state, the wires 54 are greatly withdrawn from the shredding pipe 53 and connected to the opening support section 33 via the cutting pouch 51 and the recovery pouch 2. As a result, the top portions 54A of the wires 54 are arranged at intervals along the edge of the opening portion 21 and have a circular shape for housing tissues inserted from the opening portion 21. Each of the wires 54 is sufficiently long and passes through the shredding pipe 53 in a position drawn from the opening 24A of the handle section 24 of the recovery pouch 2. This state represents a first arrangement in which the tissue can be introduced. In the initial state, the operating section 52 is not attached to the shredding pipe 53 and the end portions 98 and 99 of each wire 54 are withdrawn from the shredding pipe 53 as it is.

Figure 19:
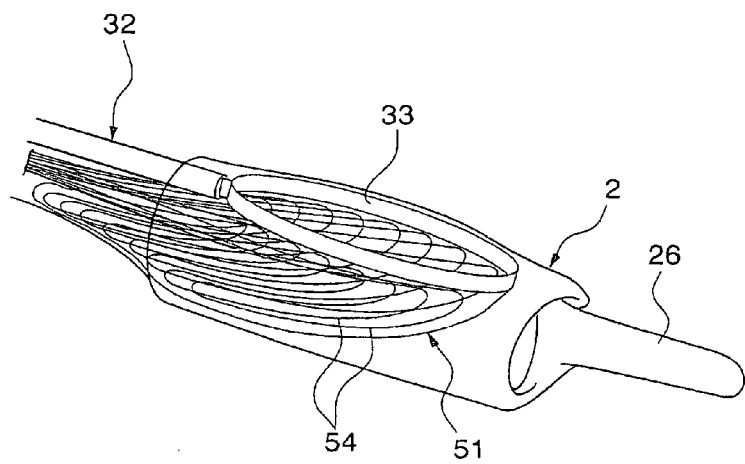
FIG. 19 is a perspective view illustrating a state in which a tissue shredding device is housed in a cover.

As shown in FIG. 19, when the recovery pouch 2 and the tissue recovering unit 3 are inserted into the cover 5, the opening support section 33 is closed and elongated, the top portion 54A of the wire 54 passing through the cutting pouch 51 is placed in the base end side, and the recovery pouch 2 is wound on the tissue recovering unit 3. Accordingly, the diameter of the recovery pouch 2 is narrowed, whereby it is possible to insert the recovery pouch 2 and the tissue recovering unit 3 into the cover 5.

Next, a method using the tissue cutting device 1 will be described. FIGS. 21 to 30, 32, and 33 illustrate perspective views so as to easily understand a description of the method.

First, a plurality of small openings such as openings having a diameter of about 14 mm is formed in the abdominal wall. An abdominal cavity is insufflated from the opening, a trocar is inserted into the opening, and an abdominoscope is inserted into an abdominal cavity via the trocar. A position of the kidney is confirmed with the abdominoscope and the kidney is removed by a forceps inserted from the other opening.

Figure 20:
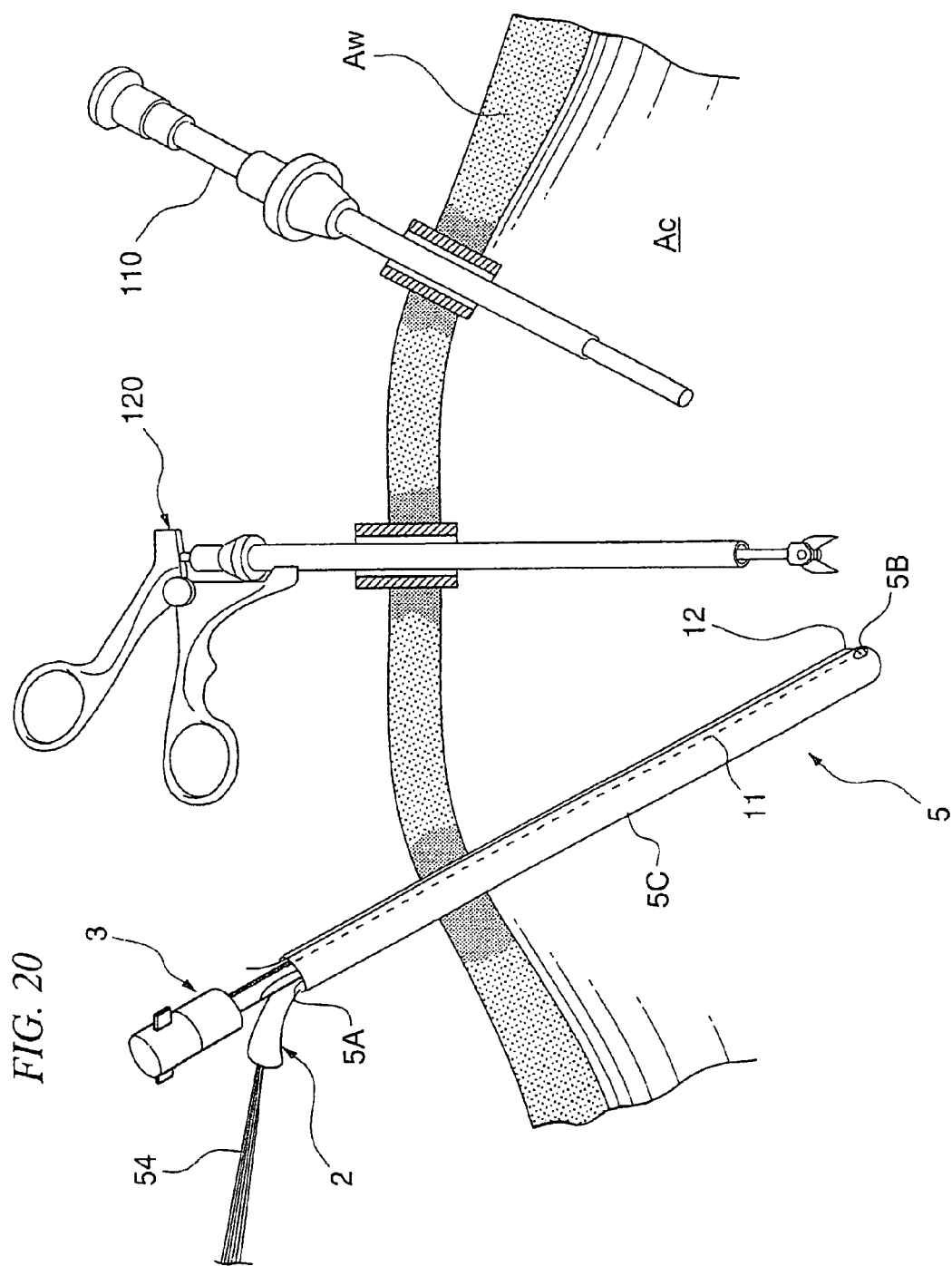
FIG. 20 is a diagram illustrating a maneuver and a diagram illustrating a state in which a tissue shredding device is inserted into an abdominal cavity.

As shown in FIG. 20, the tissue cutting device 1 housed in the cover 5 is inserted into an abdominal cavity Ac from an opening different from an abdominoscope 110 or a forceps 120. A base end portion of the cover 5, the thread 12, and the handle section 24 exposed from the cover 5 are left outside the body. The shredding pipe 53 is left outside the body while passing through the wire 54.

Figure 21:
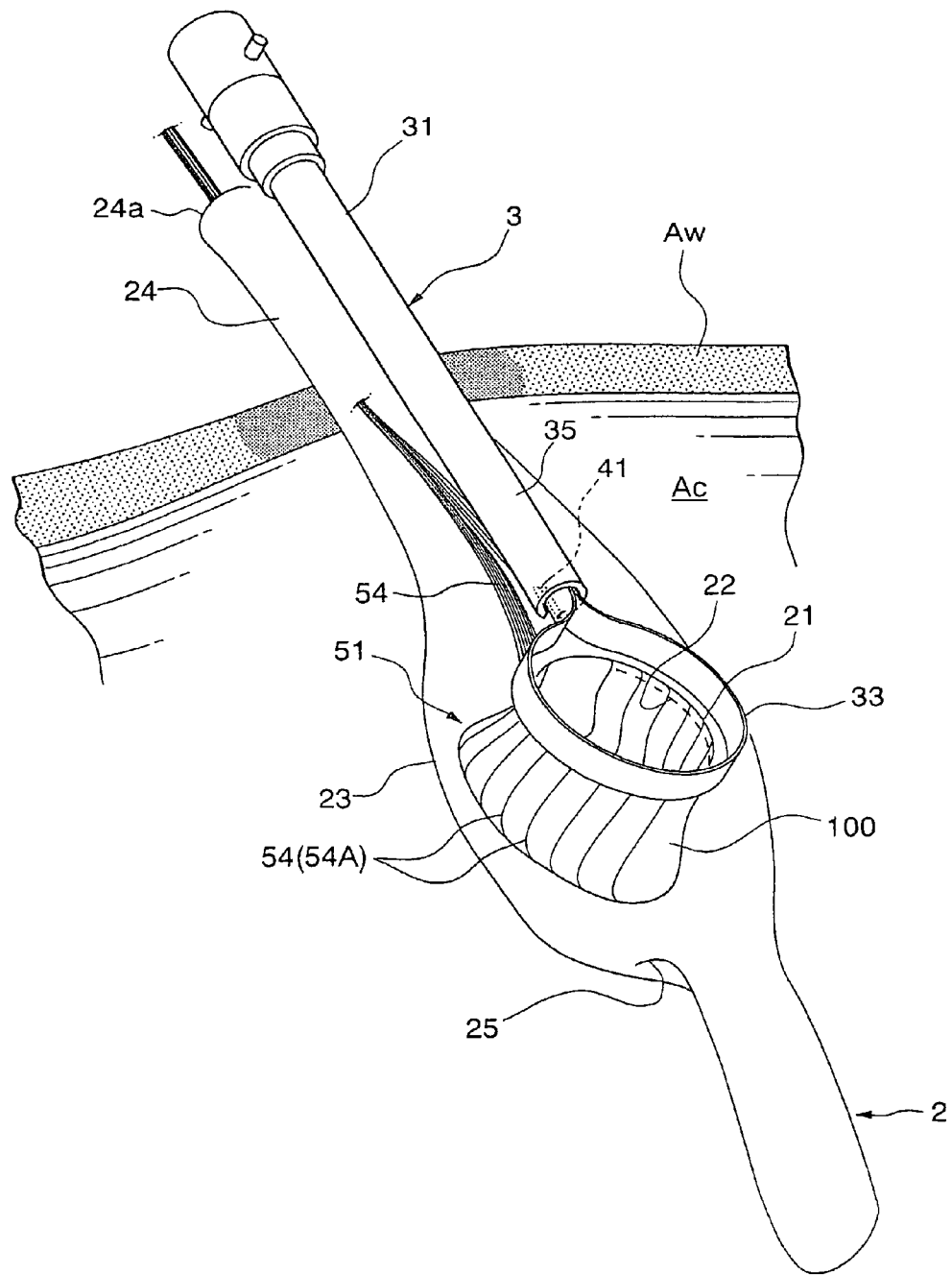
FIG. 21 is a perspective view when a cover is taken off and a recovery pouch is unfolded in an abdominal cavity.

When both ends of the thread 12 are pulled with the holding section 31 of the tissue recovering unit 3, only the cover 5 is pulled toward the outside of the patient's body. Since the front end of the opening support section 33 of the tissue recovering unit 3 hits the front end of the cover 5, the break section 11 is broken and the cover 5 is opened at the time of further pulling both ends of the thread 12. The front end of the cover 5 is removed from the opening support section 33 with the forceps 120 and the cover 5 is withdrawn to the outside of the patient's body. As shown in FIG. 21, the recovery pouch 2 is unfolded in the abdominal cavity Ac.

Figure 22:
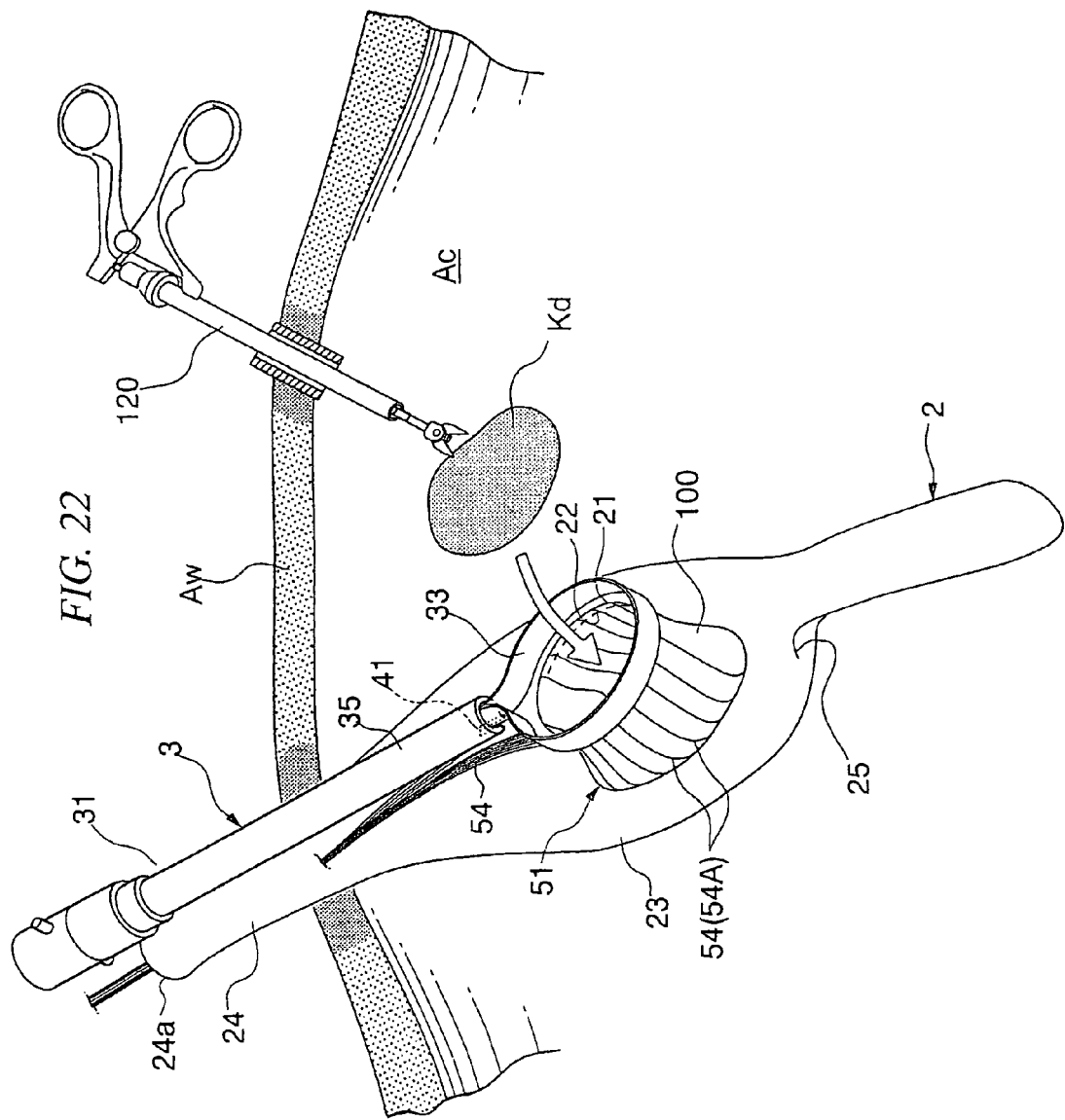
FIG. 22 is a perspective view when a kidney is inserted from an opening portion of a recovery pouch.

As shown in FIG. 22, the forceps 120 and the opening support section 33 perform a scoop action simultaneously, whereby a kidney Kd is inserted into the tissue cutting device 1 from the opening portion 21. The kidney Kd is housed in a concave space formed by the top portions 54A of the wires 54 connected to the opening portion 21. Since the wires 54 abut a bottom part of the kidney Kd, the kidney Kd does not drop. The cutting pouch 51 abuts the front end of the kidney Kd, whereby movement of the kidney Kd is restricted.

Figure 23:
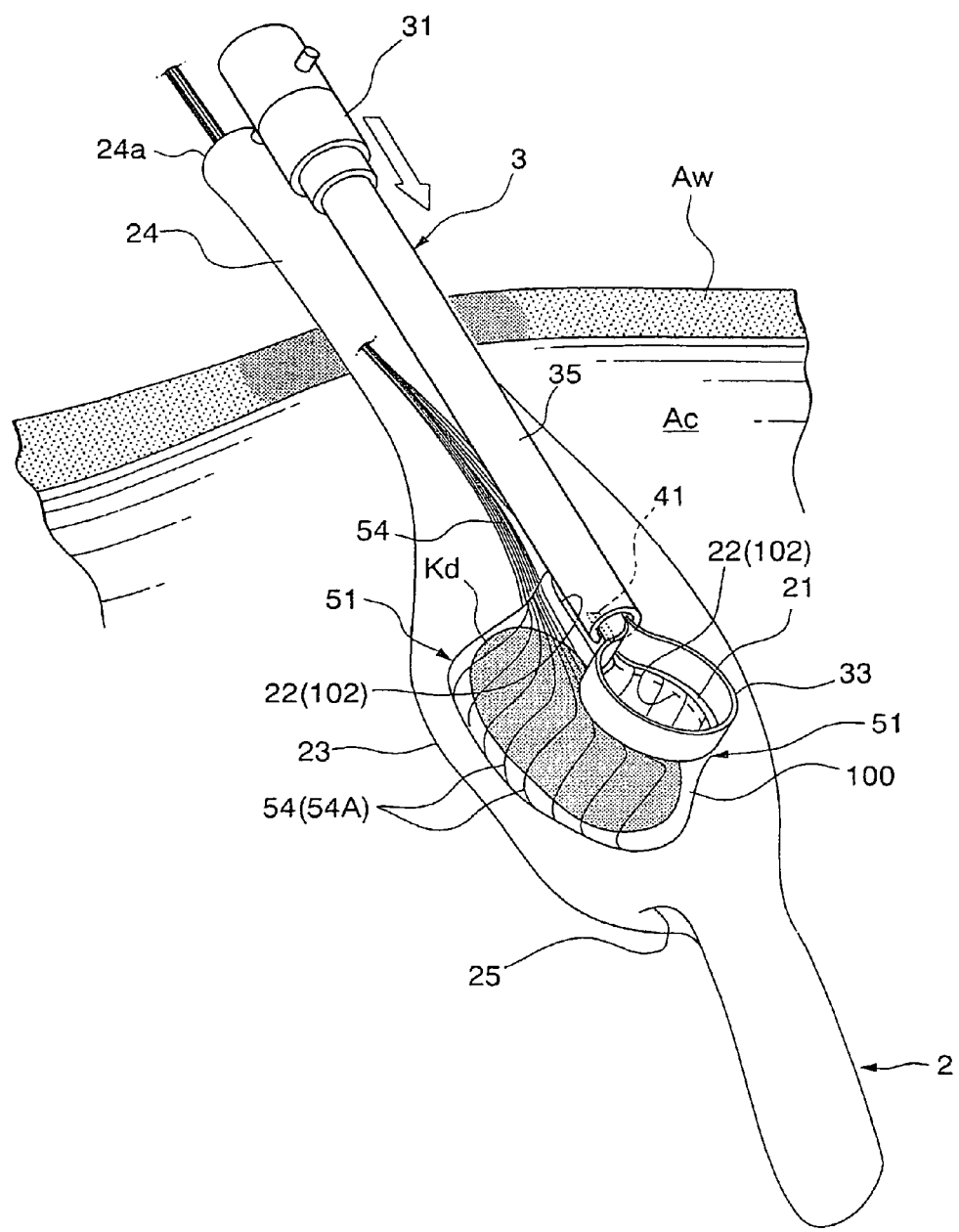
FIG. 23 is a perspective view when a break section is cut with a pouch cutting pipe of a tissue recovering unit.
Figure 24:
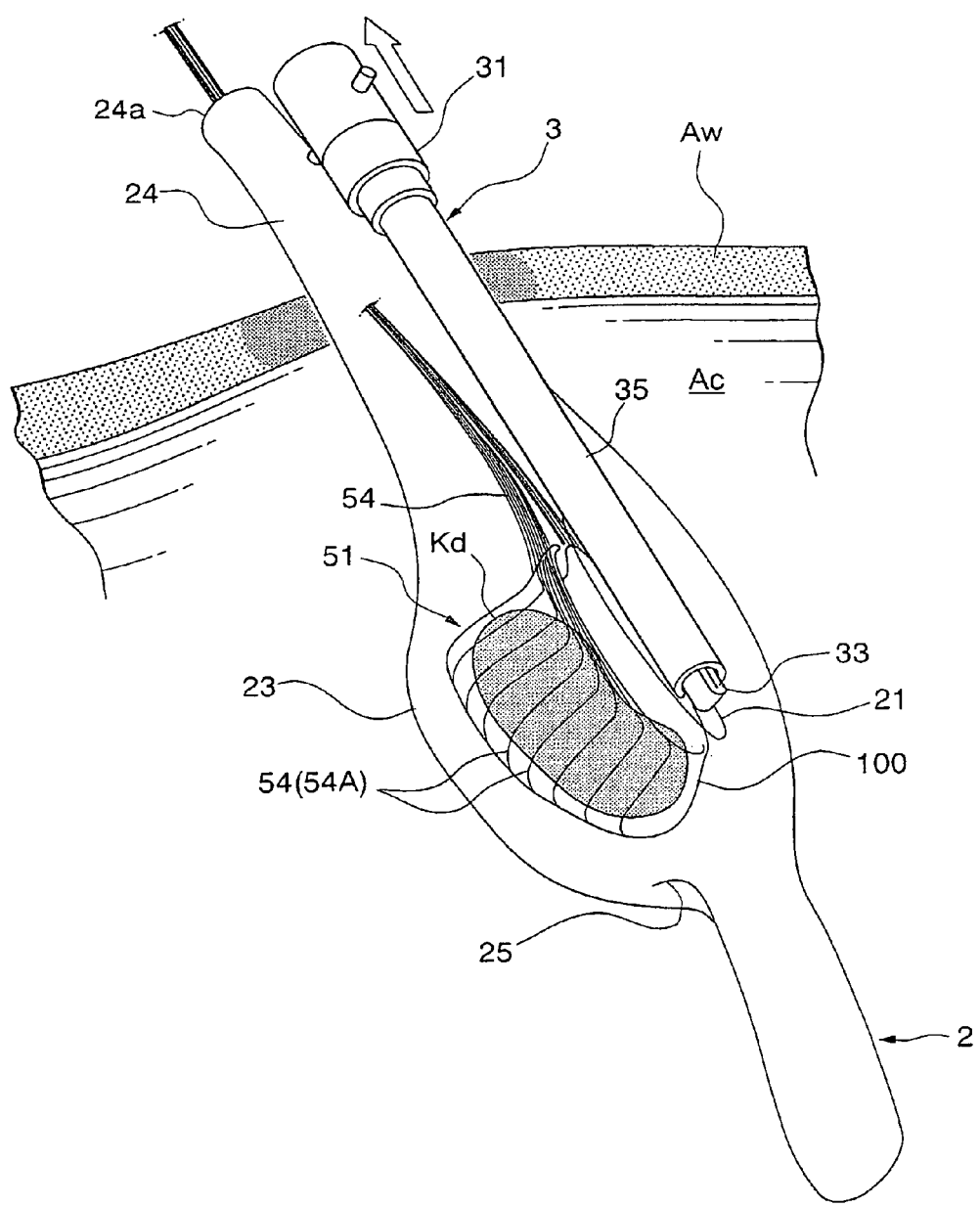
FIG. 24 is a perspective view illustrating a state in which a tissue recovering unit is separated from a recovery pouch.

Next, the kidney Kd is moved to the shredding cover section 25 in the recovery pouch 2. First, the pouch cutting pipe 35 of the tissue recovering unit 3 is pushed, and the recovery pouch 2 and the cutting pouch 51 are separated. When the pouch cutting pipe 35 is pushed, the opening support section 33 is drawn into the pouch cutting pipe 35, which is closed. As shown in FIG. 23, the break sections 22 and 102 are interposed and cut by the cutting section 41 positioned in a protrusion 36. As shown in FIG. 24, the opening support section 33 is inserted into the pouch cutting pipe 35 and the tissue recovering unit 3 is deviated from the recovery pouch 2. The cutting pouch 51 is also separated from the tissue recovering unit 3 and the recovery pouch 2. Accordingly, it becomes possible to draw only the tissue recovering unit 3 to the outside of the patient's body.

Figure 25:
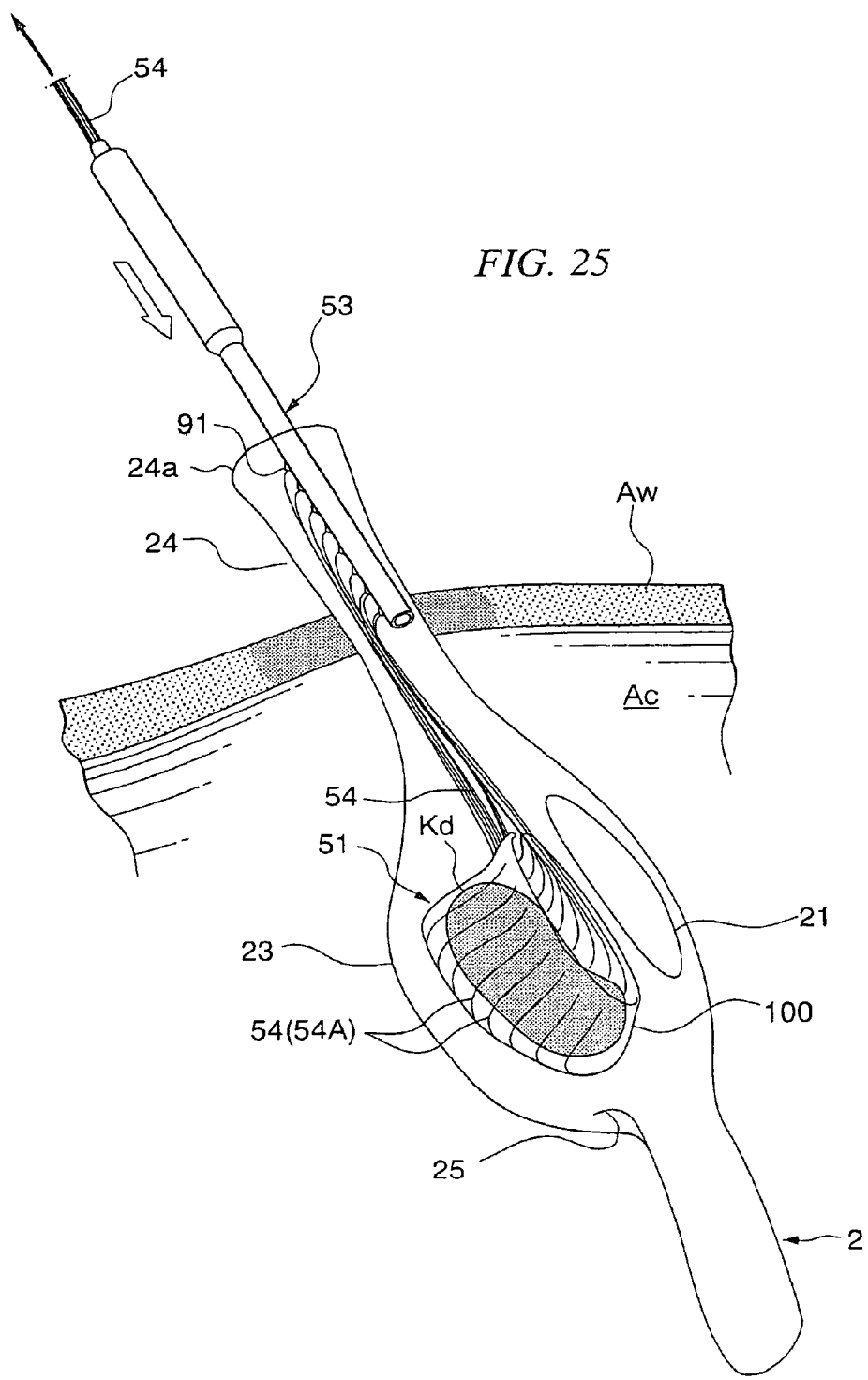
FIG. 25 is a perspective view when a shredding pipe is inserted.
Figure 26:
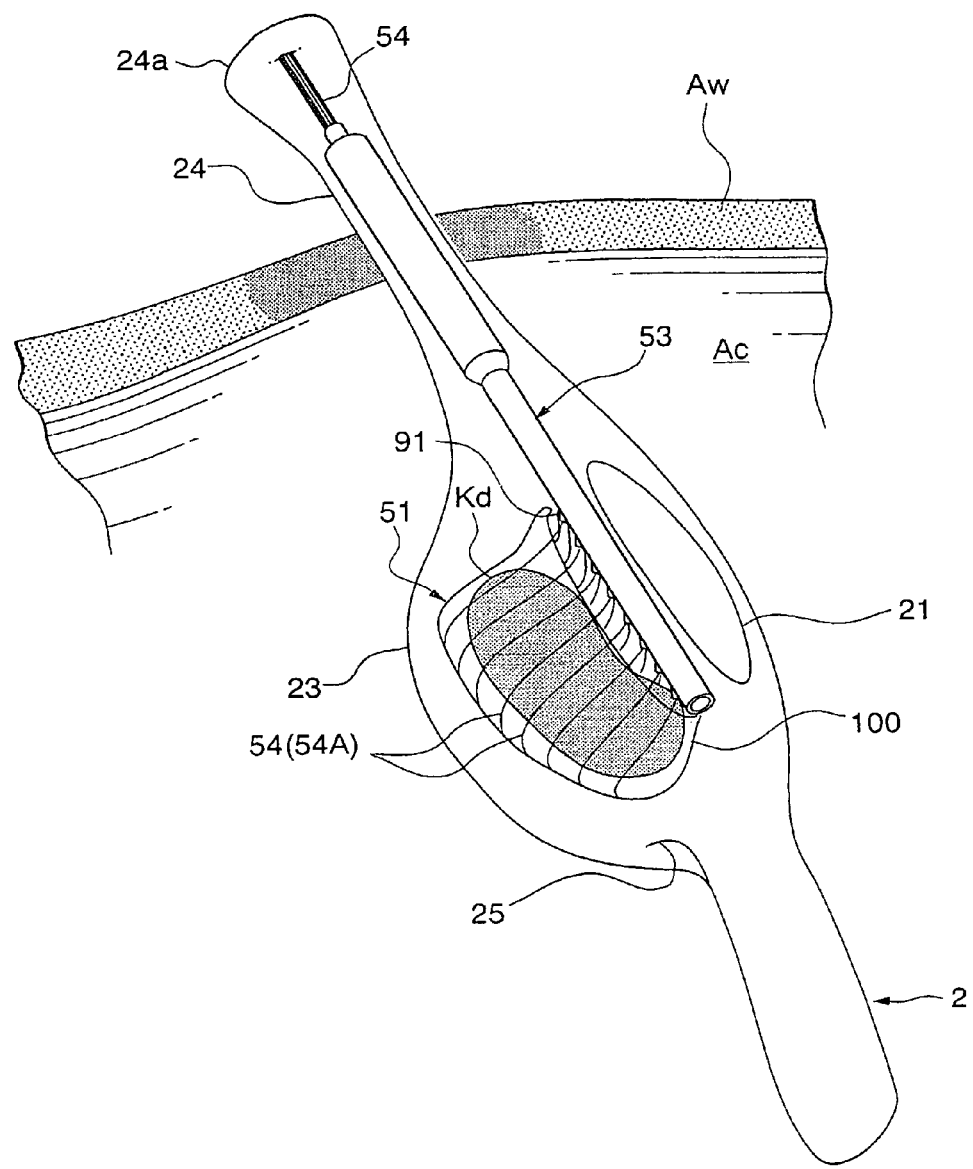
FIG. 26 is a perspective view when wires of a tissue shredding device are arranged in a second arrangement and a kidney is housed in a loop part formed of a shredding pipe and wires.

Next, the tissue shredding device 4 is assembled so as to shred the kidney Kd. As shown in FIG. 25, the shredding pipe 53 is inserted into the recovery pouch 2 by holding up the wires 54. As shown in FIG. 26, a large-diameter part of the shredding pipe 53 is inserted into an opening of an abdominal wall Aw. A large-diameter part of the base end side of the shredding pipe 53 serves an airtight holding section, whereby an insulating gas does not leak outside the body. The kidney Kd is disposed opposite to the front end portion of the shredding pipe 53 and a loop shape formed by the wires 54 is disposed by substantially imitating intervals of the guide members 91. In other words, the kidney Kd is disposed in a space formed by the each wires 54 disposed substantially at even intervals and the shredding pipe 53.

Figure 27:
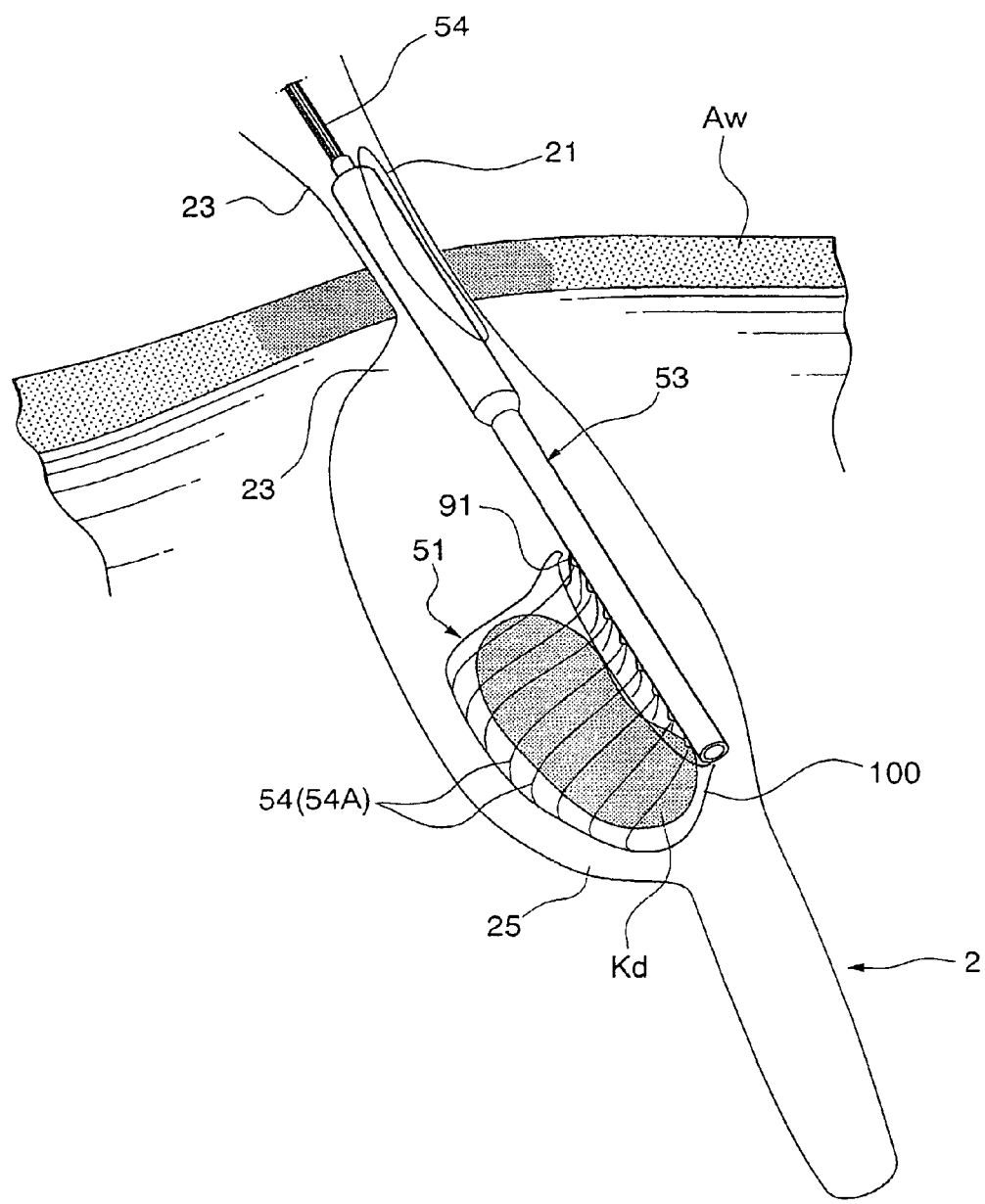
FIG. 27 is a perspective view when an opening portion of a recovery pouch is withdrawn outside a patient's body.
Figure 28:
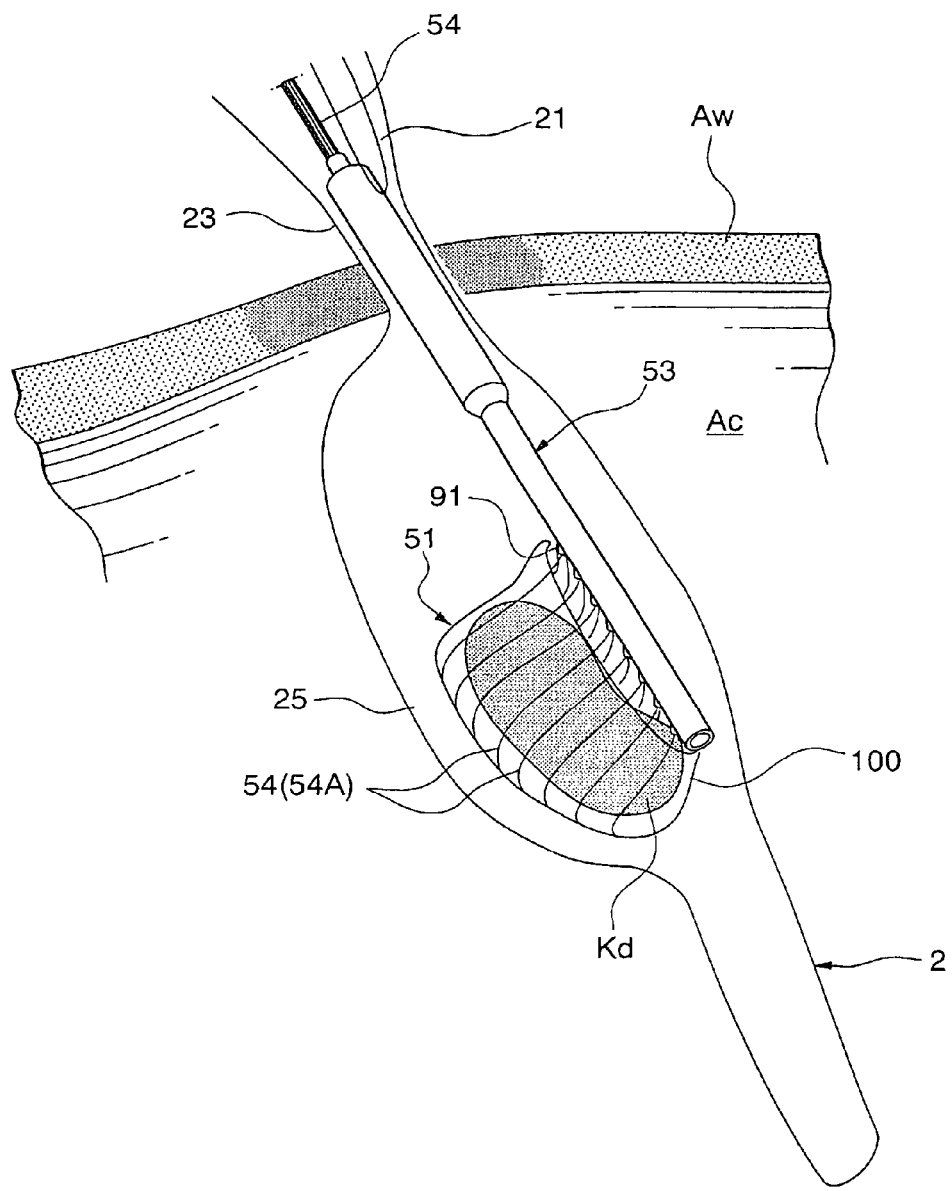
FIG. 28 is a perspective view illustrating a state in which an opening portion of a recovery pouch is drawn outside a patient's body.

As shown in FIG. 27, the handle section 24 of the recovery pouch 2 is pulled and the opening portion 21 of the recovery pouch 2 is drawn outside the body while the shredding pipe 53 is held. As shown in FIG. 28, the front end portion of the recovery pouch 2 hits the shredding pipe 53 and a bent-back part of the shredding cover section 25 is drawn and unfolded in the abdominal cavity Ac.

Figure 29:
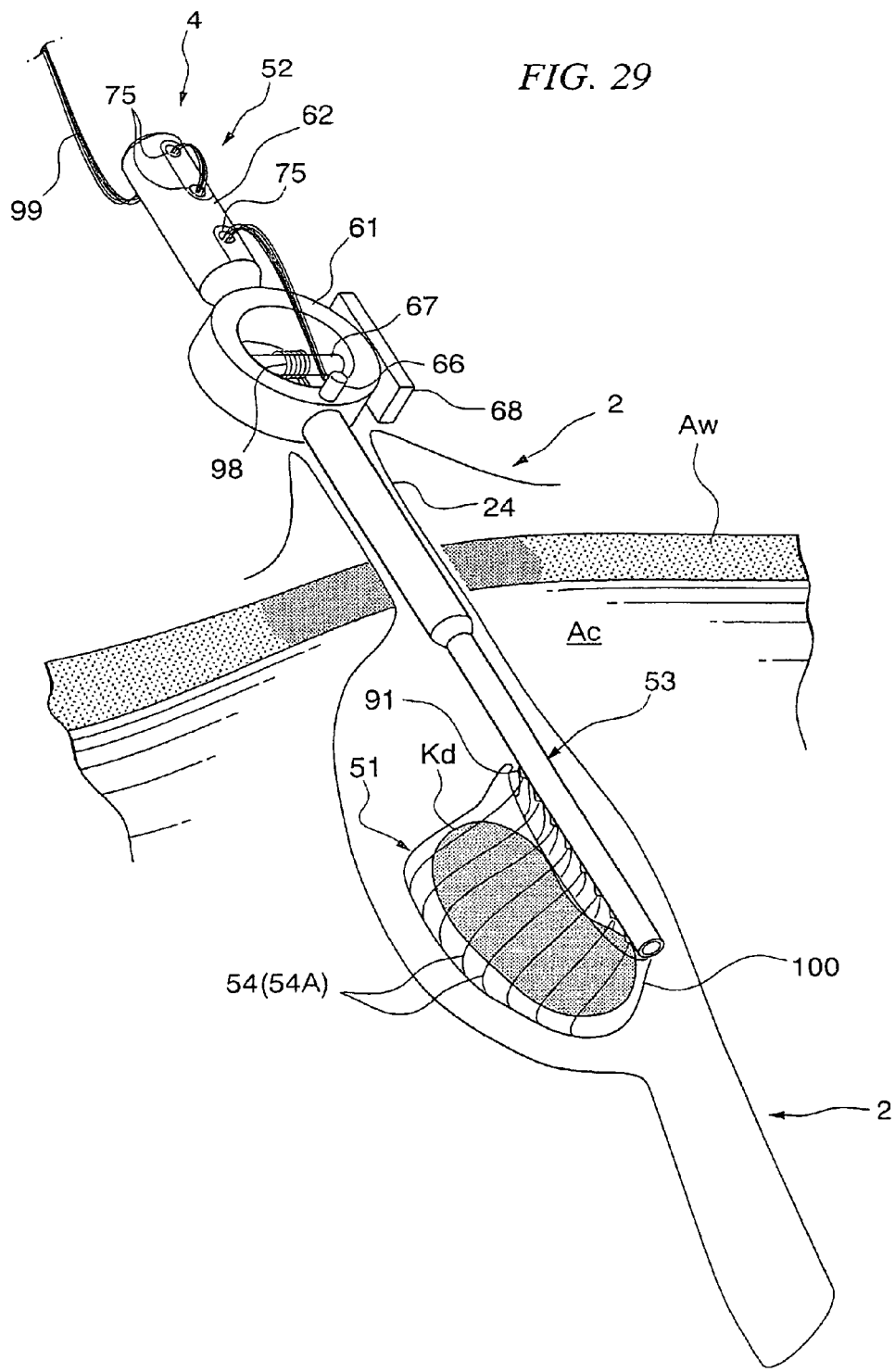
FIG. 29 is a perspective view illustrating a state in which an operating section is attached to a shredding pipe.

As shown in FIG. 29, the operating section 52 of the tissue shredding device 4 is fixed in the shredding pipe 53. The first end portion 98 of the wire 54 passes through the shaft 67 and is fixed in the shaft 67. The second end portion 99 of the wire 54 passes through the fixation section 75 of the grip 62 in a crank shape and is fixed in the fixation section 75. When the first end portion 98 and the second end portion 99 are bound up in advance, fixation work becomes easier. In addition, the first end portion 98 and the second end portion 99 are difficult to bind up in the proximal side at the time of drawing the wire 54 later. When the first end portion 98 and the second end portion 99 are color-coded each other or a shape is changed by bending any one of them, it is easy to distinguish them.

The top portions 54A of the wires 54 are opposed to the shredding pipe 53 and are arranged in a longitudinal direction of the shredding pipe 53. The top portions 54A of the wires 54 take a second arrangement in which the kidney Kd is disposed inside the loop geometry of the wire 54.

Figure 30:
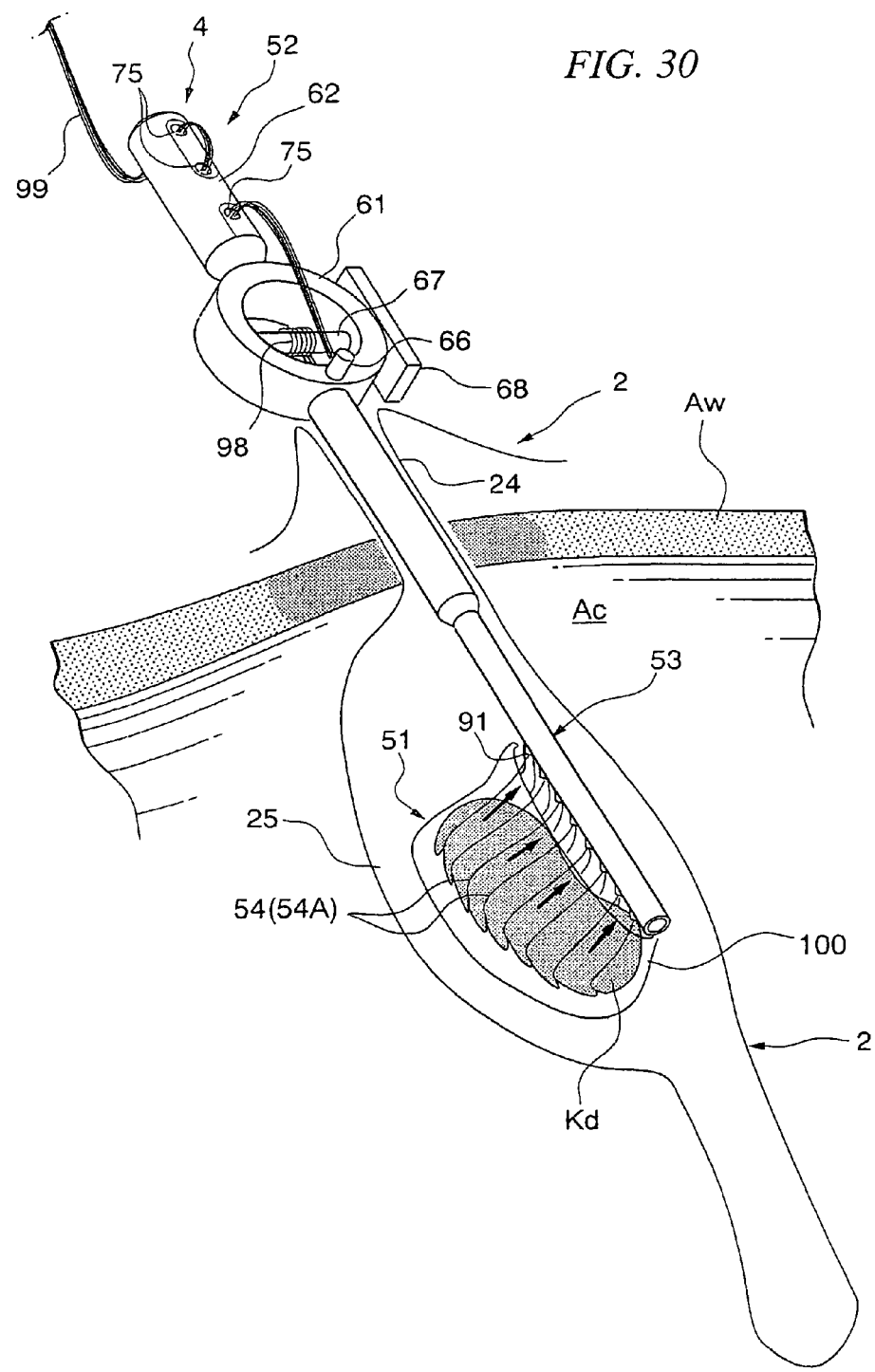
FIG. 30 is a perspective view when a kidney is shredded by turning a handle.

As shown in FIG. 30, when the handle 68 is turned, the wire 54 is drawn into the shredding pipe 53. The end portion 98 fixed in the shaft 67 is pulled, whereby a part of the wire 54 withdrawn outside the shredding pipe 53 is shortened and is closely contacted to an outer periphery of the kidney Kd. Accordingly, the kidney Kd is positioned and held in the tissue shredding device 4. When the wire 54 is further drawn into the shredding pipe 53, the loop shape formed by the wire 54 is equal to or smaller than an external diameter of the kidney Kd, whereby the kidney Kd begins to be slowly shredded from the outer periphery thereof.

Figure 31:
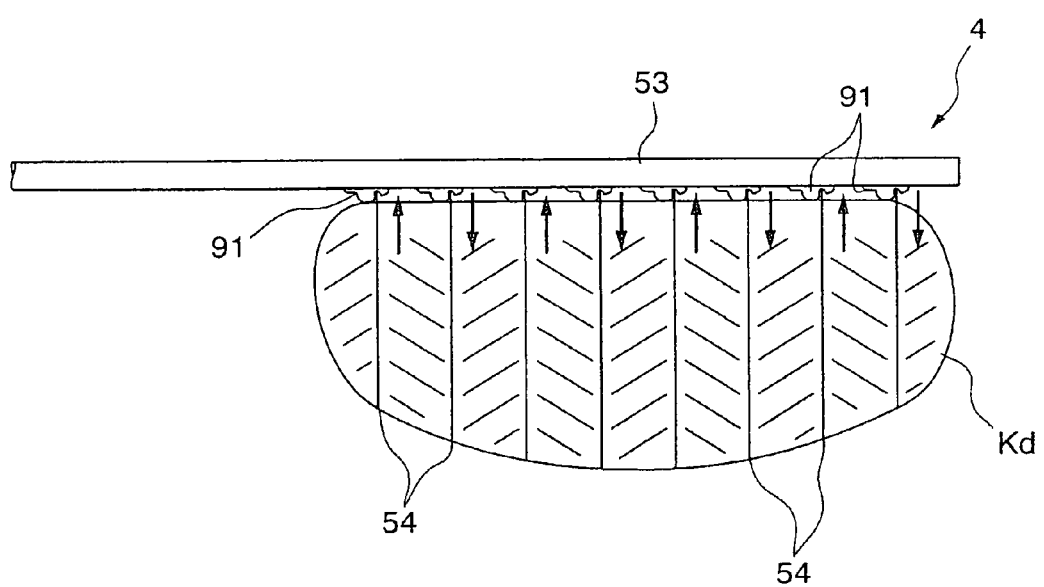
FIG. 31 is a diagram illustrating a state in which a kidney is cut.

For example, the wires 54 passing through the odd-numbered openings 80 are pulled in a direction indicated by an arrow. On the contrary, the wires 54 passing through the even-numbered openings 80 are pulled to the opposite end. In other words, the plurality of wires 54 disposed in a longitudinal direction of the kidney Kd is pulled in an opposite direction alternatively, whereby applying a reverse-direction tensile force on the kidney Kd which serves as a momentum for shredding the tissue. The kidney Kd is shredded based on the momentum. As shown in FIG. 31, since the tensile force can be applied to a surface of a tissue which is difficult to cut such as a gerota fascia on a surface of a liver, the tissue can be also cut. A force required to draw the wires 54 can be reduced to half in comparison with a force required to draw both ends of the wires 54 by drawing one end thereof.

The kidney Kd is pushed by the shredding pipe 53 while the kidney Kd is shredded, but since the wires 54 slip into the groove 94 of the guide member 91 shown in FIG. 15, there is no possibility that the wires 54 are pushed by the kidney Kd and the shredding pipe 53, whereby the wires 54 are not pulled. Since the wire 54 of one end portion 98 slips into the groove 95 while the wires 54 are drawn into the shredding pipe 53 from the guide members 91, there is no possibility that the wire 54 of the end portion 98 is interposed between the wire 54 of the other fixed end portion 99 and the guide member 91, whereby the wires 54 are not pulled. Even though the other end portion 99 is inserted into the groove 95, it is possible to prevent an interference with the wire 54 of the one end portion 98. Accordingly, the kidney Kd is shredded in a third arrangement in which the top portions 54A of the wires 54 withdrawn in the loop shape are completely drawn into the shredding pipe 53.

Figure 32:
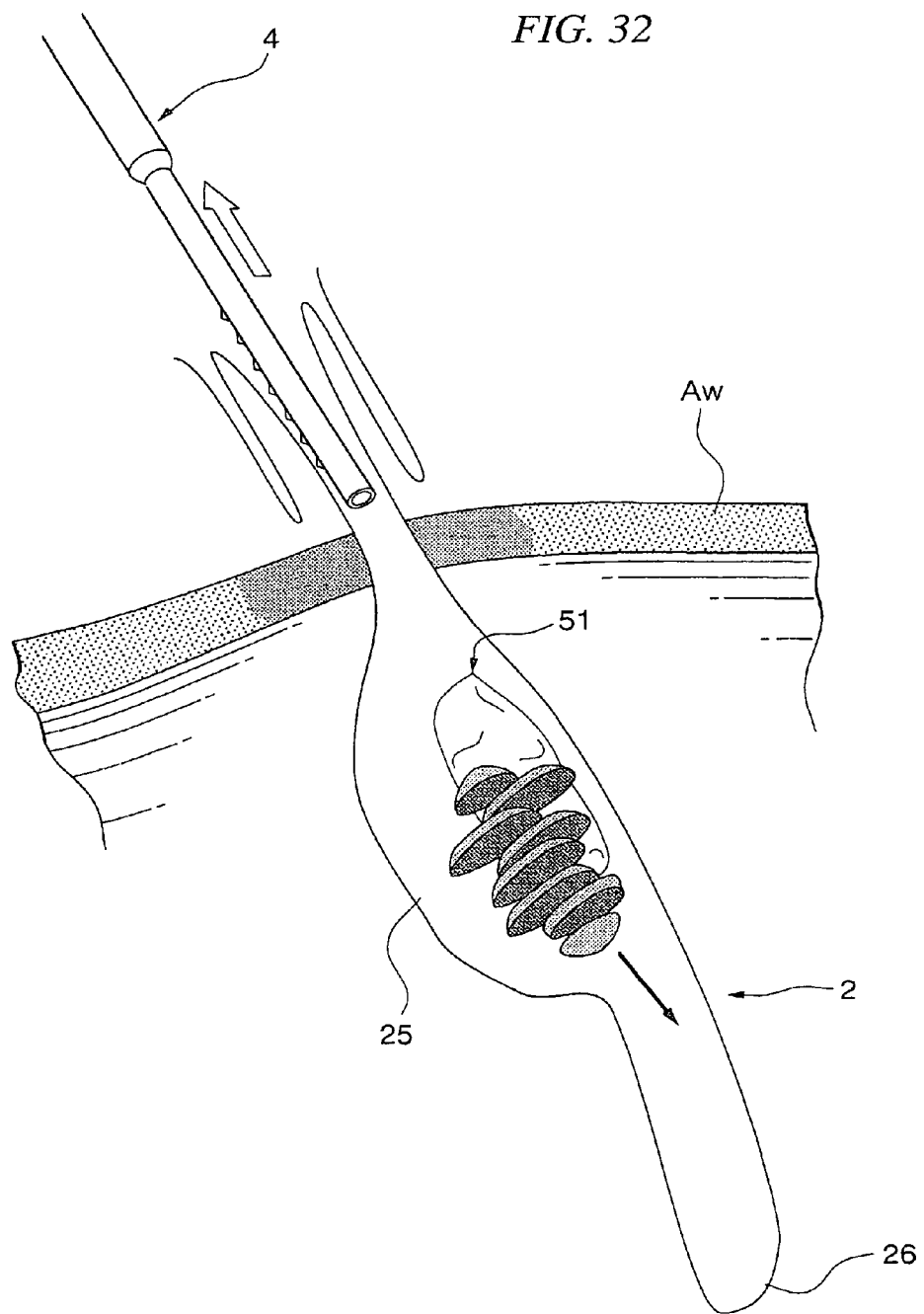
FIG. 32 is a perspective view when wires of a tissue shredding device are arranged in a third arrangement and a tissue shredding device is pulled outside a patient's body after shredding the tissue.
Figure 33:
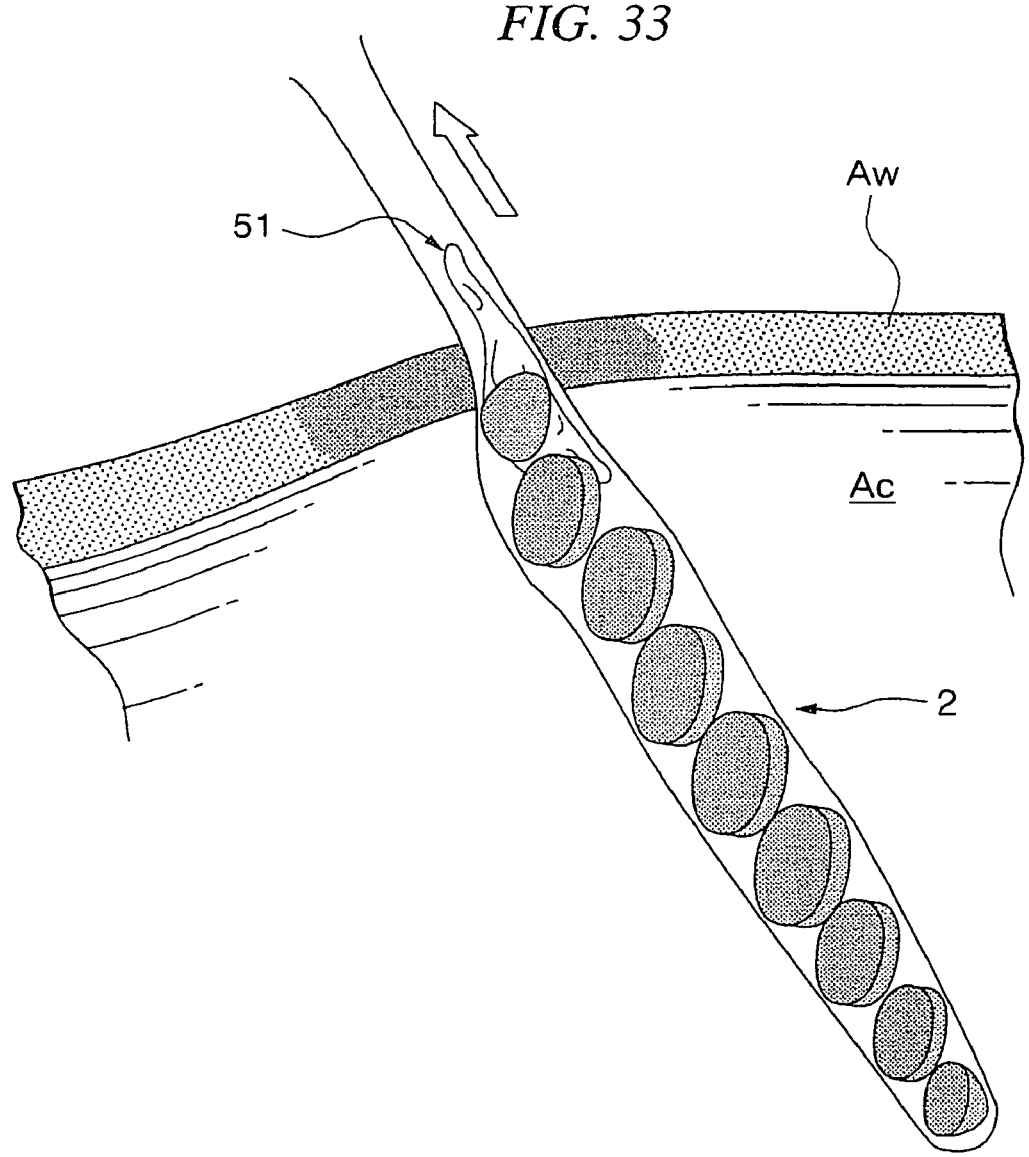
FIG. 33 is a perspective view when a cut kidney is extirpated outside a patient's body for each recovery pouch.

As shown in FIG. 32, when the shredding pipe 53 is pulled out from the recovery pouch 2, the cutting pouch 51 and pieces of the shredded kidney Kd are left in the recovery pouch 2. The pieces drop to the extirpation section 26 from a gap between the cutting pouch 51 and the recovery pouch 2. When the recovery pouch 2 is pulled out, the shredded kidney Kd is extirpated outside the body as shown in FIG. 33.

In the embodiment, the tissue can be inserted into the space formed by the wires 54 from a direction substantially orthogonal to an insertion direction into the abdominal cavity Ac. It is difficult to insert the tissue in an arrangement direction of the wires 54 in a limited space of the abdominal cavity Ac, but in the embodiment, it is possible to easily and reliably arrange the tissue in the wires 54.

Since the shredding pipe 53 is disposed opposite to the tissue and the plurality of wires 54 can be arranged in a longitudinal direction of the tissue at the time of shredding the tissue, it is possible to prevent displacement of the tissue. Since an elongated tissue can be shredded into small pieces, extirpation becomes easier.

Since the wire 54 is withdrawn from the same opening 80 of the shredding pipe 53 to form a loop, the wires 54 can be completely drawn into the shredding pipe 53. As the result, it is possible to reliably shred the tissue. Since the wires 54 slip into the groove 94 of the guide member 91, there is no possibility that the wires 54 are interposed between the tissue and the shredding pipe 53, whereby the wires 54 are not pulled. Similarly, since the groove 95 is provided inside the guide member 91, it is possible to prevent the interference with the wires 54 and to completely draw the wires 54 into the shredding pipe 53.

Since the housing section 23 having the opening portion 21 and the shredding cover section 25 not having the opening portion 21 are provided in the recovery pouch 2, fragments of the tissue are not disseminated in the patient's body at the time of shredding the tissue in the shredding cover section 25. Since the thin extirpation section 26 is provided in front of the shredding cover section 25 and houses a shredded tissue, it is possible to reduce an external diameter at the time of extirpating the shredded tissue outside the body, whereby extirpation of the shredded tissue becomes easier.

Here, modified examples of the embodiment are described.

Figure 34:
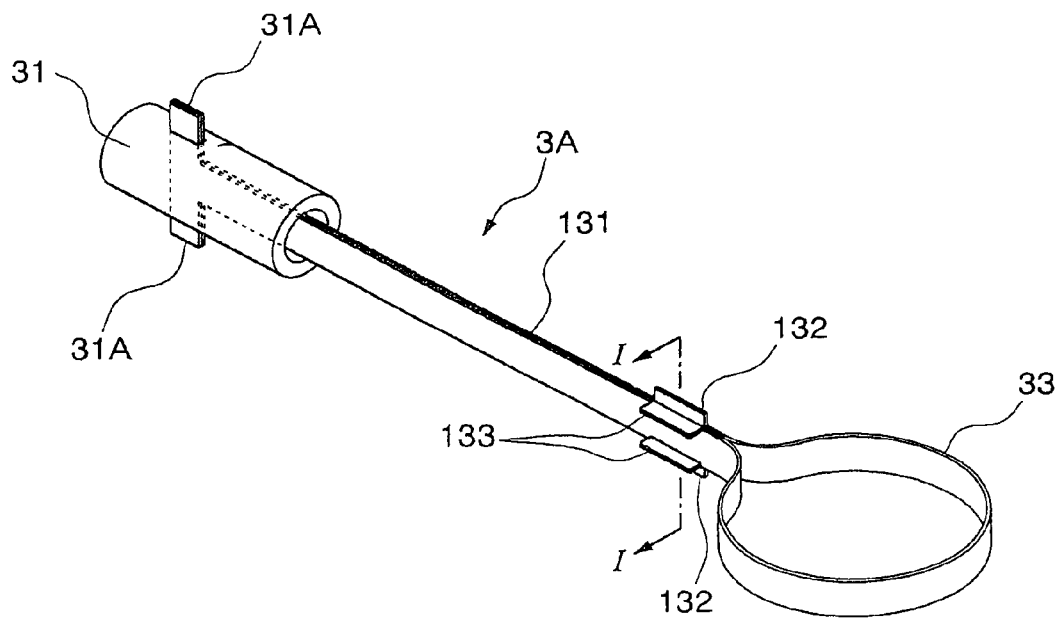
FIG. 34 is a diagram illustrating a modified example of a tissue recovering unit.
Figure 35:
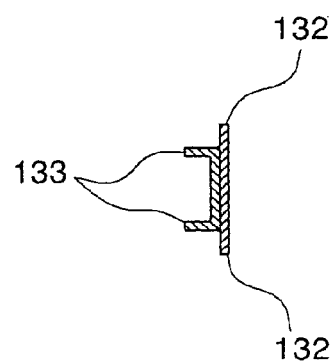
FIG. 35 is a cross-sectional view taken along line 1-1 of FIG. 34.

The tissue recovering unit 3 shown in FIG. 34 extends a plate forming the opening support section 33 and incorporates an insertion section 131. The base end of the opening support section 33 is molded in a rugby ball shape by welding. A protrusion portion 132 formed by extension of the plate is provided in a front end of the insertion portion 131. The protrusion portion 132 is inserted into the slits 40 (see FIG. 8) of the pouch cutting pipe 35. The protrusion portion 132 serves to prevent rotation of the pouch cutting pipe 35 and guide advancing and retreating of the pouch cutting pipe 35. As shown in FIG. 35, a part 133 overlapped with the protrusion portion 132 extends in a direction substantially orthogonal to the protrusion portion 132. The part 133 prevents the tissue recovering unit 3A from being axially deviated from the pouch cutting pipe 35.

Figure 36:
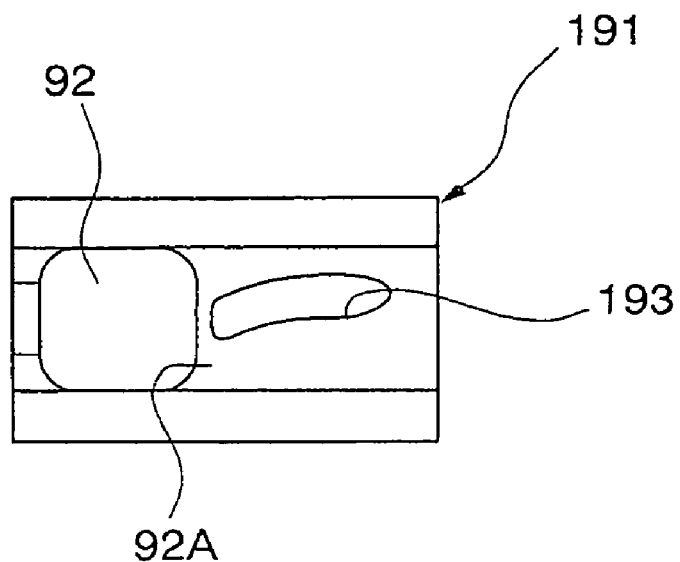
FIG. 36 is a diagram illustrating a modified example of a guide member.
Figure 37:
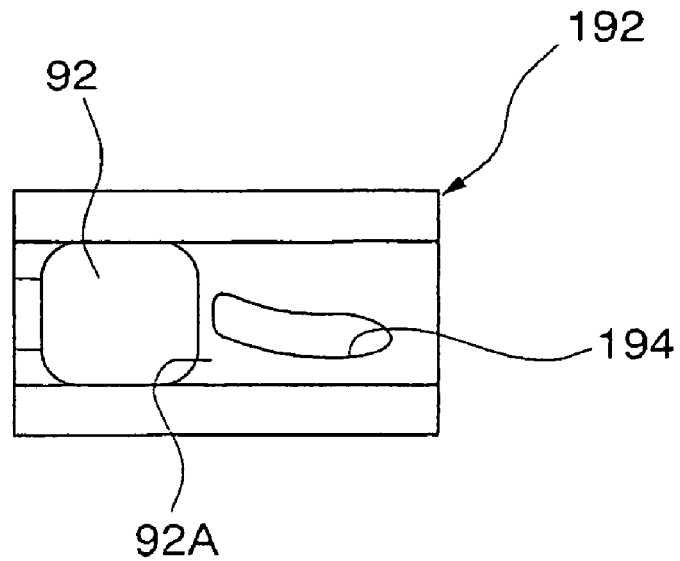
FIG. 37 is a diagram illustrating a modified example of a guide member.

FIGS. 36 and 37 illustrate a modified example of guide members attached to the shredding pipe 53 of the shredding device 4. In guide members 191 and 192, curved grooves 193 and 194 are carved in the insertion hole 92. The grooves 193 and 194 are provided in positions in which centers of base ends are offset from center lines of the guide members 191 and 192, respectively. Front end portions of the grooves 193 and 194 are curved in a direction opposite to an offset direction. The grooves 193 and 194 are designed in a form following optimum routes of the wires 54 when a force is applied to the wires 54. The guide members 191 and 192 are disposed in a direction in which the end portion 98 side of the wire 54 passes through the grooves 193 and 194. As the result, the guide member 191 shown in FIG. 36 and the guide member 192 having an opposite curved direction, which is shown in FIG. 37, are alternatively mounted. In the guide members 191 and 192, since the grooves 193 and 194 are curved in a direction in which the wires 54 are pulled, it is easy to pull the wires 54. Since the wires 54 which are drawn into the shredding pipe 53 from an opposite side of the curved direction, that is, the side of the end portion 99 fixed in the grip 62 passes over the end portion 98 inserted into the groove 193 or 194, it is difficult for the wires 54 to interfere with each other, thereby reducing a force required to draw the wires 54. On the contrary, even when the end portion 99 of the wires 54 in a side fixed in the grip 62 is inserted into the groove 193 or 194 and the end portion 98 in a side pulled passes over the end portion 99 inserted into the groove 193 or 194, the wires 54 are difficult to interfere with each other, and it is possible to obtain the same effect.

Figure 38:
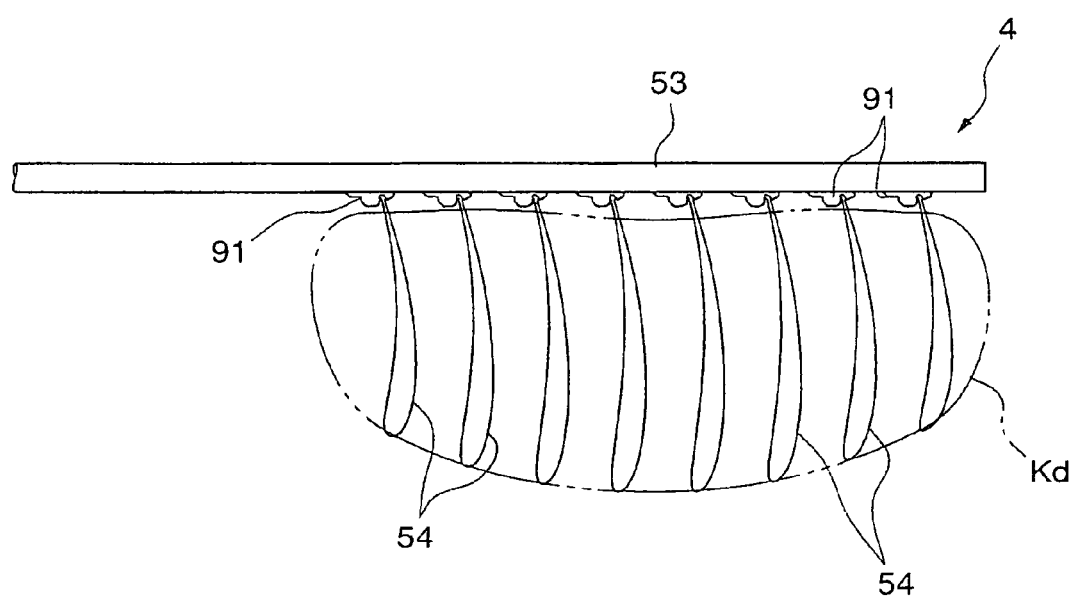
FIG. 38 is a diagram illustrating a modified example of an amount of drawn wires in a second arrangement.

As shown in FIG. 38, an amount of the drawn wires 54 may be changed for each site. In this case, a short front end, a long center, and a short proximal side are withdrawn in accordance with a shape of the kidney Kd and a plurality of top portions 54A is arranged on a curve. In the above-mentioned embodiment, the wires 54 are withdrawn substantially in the same amount and the plurality of top portions 54A is arranged in a straight line, but it is possible to further prevent displacement of the kidney Kd and the wires 54 by changing the drawing amount.

Figure 39:
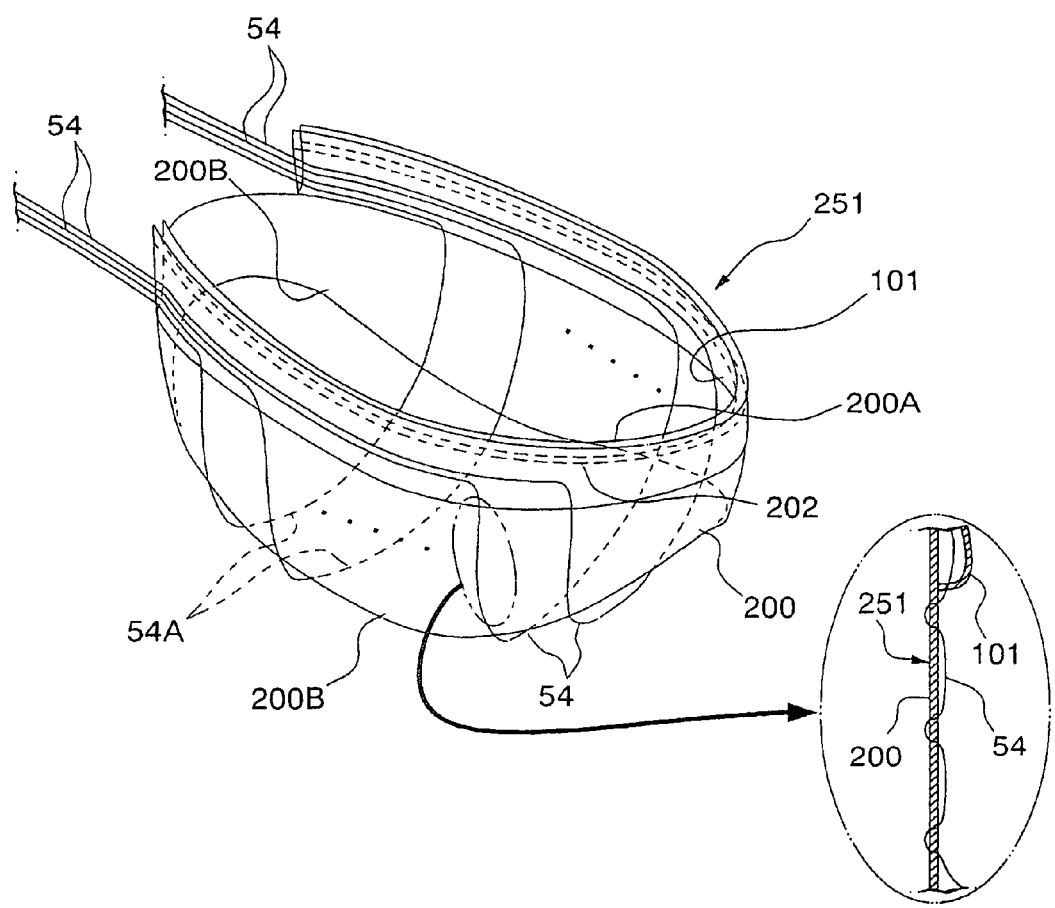
FIG. 39 is a diagram illustrating a modified example of a cutting pouch.

As shown in FIG. 39, a cutting pouch 251 may be formed of a circular member 200. The circular member 200 has a double structure in which a strip-shaped member 101 is attached to one edge portion 200A by thermal compression and the like. The wires 54 pass through the portion of the double structure. The break section 102 formed of the perforation is provided in the portion of the double structure. The one edge portion 200A is fixed in the recovery pouch 2 in a state where an opening of the cutting pouch 251 is connected to the opening portion 21. An end portion of a proximal side of the circular member 200 is notched so that the wires 54 can be withdrawn. The wires 54 are inserted into the portion of the double structure from the end portion in which the proximal side is notched and pass in a circumferential direction of the cutting pouch 251. The wires 54 are bent toward the other edge portion 200B from the one edge portion 200A at predetermined intervals. The wires 54 cross the other edge portion 200B after passing through an inside and an outside of the circular member 200 alternatively. The top portion 54A of the wire 54 is disposed in a crossing part. In the circular member 200, a central portion of the other edge portion 200B is longer than the front end and the proximal side of the other edge portion 200B in accordance with arrangement of the wires 54 shown in FIG. 39. However, lengths of the other edge portion 200B may be substantially constant irrespective of the site.

In the cutting pouch 251, since an end portion of a proximal side is closed except for a part in which the wires 54 are withdrawn, it is possible to prevent the kidney Kd from straying in the proximal side. Since the edge portion 200B at the opposite side is opened, cut pieces of the kidney Kd can be dropped in the same manner as above.

Since arrangement of the wires 54 is held by the shape of the other edge portion 200B, it is possible to hold a state in which the plurality of top portions 54A is arranged on the curve even at the time of shifting to the third arrangement from the second arrangement. It is possible to hold the arrangement state shown in FIG. 38 at the time of extending an edge portion 100B of the cutting pouch 51 in the same manner as above.

Figure 40:
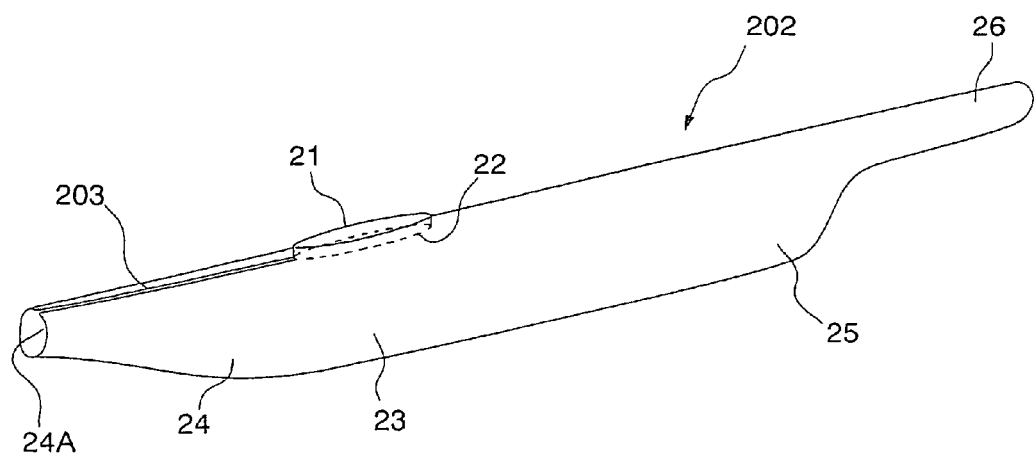
FIG. 40 is a diagram illustrating a modified example of a recovery pouch.
Figure 41:
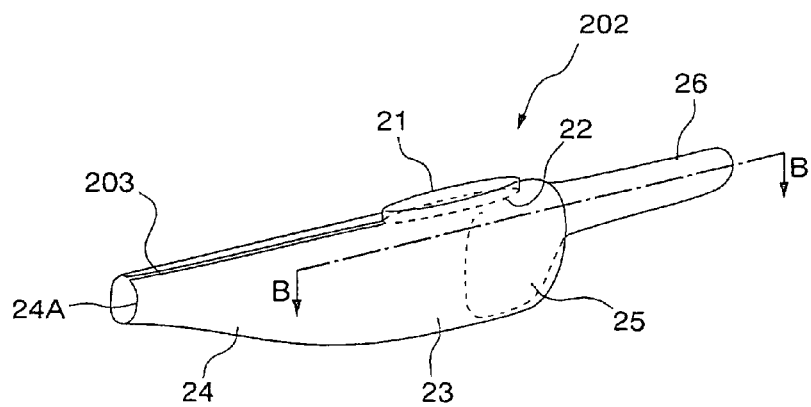
FIG. 41 is a diagram illustrating a state in which a recovery pouch shown in FIG. 40 is folded.

As shown in FIGS. 40 and 41, a slit 203 extending from the opening 24A of the handle section 24 to the opening 21 of the housing section 23 is formed in a recovery pouch 202. By using the recovery pouch 202, it is possible to prevent interference of the recovery pouch 202 and the handle 68 at the time of mounting the handle 68 of the shredding device 4 on the shredding pipe 53 after withdrawing the opening 21 outside the body as shown in FIG. 29.

The shredding pipe 53, the operating body 61, the grip 62, and the handle 68 of the operating section 52 may be made of insulated members. The wires 54 may be energized.

It is possible to configure the tissue shredding device by appropriately combining the above-mentioned modified examples.

Although exemplary embodiments of the invention have been described hitherto, the invention is not limited by the above description, but by only the scope of the appended claims.

What is claimed is:

1. A tissue cutting device comprising:
    a shredding pipe in which a plurality of opening portions is formed in a longitudinal direction of the shredding pipe;
    a plurality of wires which form a plurality of loop portions, respectively, each of the plurality of loop portions being extended from a corresponding one of the plurality of opening portions; and
    an operating section which gives a drawing force to the elongated member, the drawing force applying a reverse-direction tensile force on a tissue which is housed inside a space defined by the plurality of loop portions and comes into contact with at least two adjacent loop portions of the plurality of loop portions so that pulling directions of the at least two adjacent loop portions are opposite to each other.

2. The tissue cutting device according to claim 1, wherein virtual planes along the at least two adjacent loop portions are substantially parallel to each other.

3. The tissue cutting device according to claim 1, wherein the operating section draws the plurality of loop portions into the shredding pipe so that pulling directions of all adjacent loop portions of the plurality of loop portions are opposite to each other.

4. The tissue cutting device according to claim 1, wherein the operating section draws all of the plurality of loop portions.

5. The tissue cutting device according to claim 1, wherein a guide member is attached to the opening portion and grooves into which the loop portions can be inserted are formed in positions substantially orthogonal to a longitudinal direction of the shredding pipe in the guide member.

6. The tissue cutting device according to claim 5, wherein a concave portion into which only one elongated member can be inserted is formed toward a base end of the shredding pipe in the guide member.

7. The tissue cutting device according to claim 1, wherein:
   each of the plurality of wires is bent back at an outside of the shredding pipe, and drawn into the shredding pipe from the corresponding one of the plurality of opening portions;
   each of the plurality of wires includes a first end portion which is adapted to be fixed in relation to the shredding pipe and a second end portion which is adapted to be drawn into the shredding pipe; and
   the plurality of wires are arranged so that, when the plurality of wires are drawn into the shredding pipe, a pulling direction of one of the plurality of wires is opposite to a pulling direction of an adjacent one of the plurality of wires which is adjacent to the one wire.

8. The tissue cutting device according to claim 7, wherein the operating section includes:
   a shaft to which the first end portions of the at least two adjacent loop portions are fixed;
   a fixation section to which the second end portions of the at least two adjacent loop portions are fixed; and
   a mechanism which operates the fixation section to draw the second end portions into the shredding pipe.

9. The tissue cutting device according to claim 8, wherein:
   the first end portions of all of the plurality of loop portions are fixed to the shaft of the operating section; and
   the second end portions of all of the plurality of loop portions are fixed to the fixation section of the operating section.

10. The tissue cutting device according to claim 1, wherein the tissue cutting device is capable of being switched between one of a first arrangement in which the plurality of loop portions are extended from the shredding pipe so that a tissue can be introduced toward top portions of the plurality of loop portions, a second arrangement in which the top portions of the plurality of loop portions are arranged to oppose the shredding pipe, and a third arrangement in which the plurality of loop portions are drawn into the opening portions.

11. The tissue cutting device according to claim 10, further comprising a flexible strip-shaped member arranging the top portions of the loop portions in the first arrangement.

12. The tissue cutting device according to claim 10, further comprising a flexible and circular member arranging the top portions of the loop portions in the first arrangement,
   wherein the top portions are arranged in a position crossing an opening of the circular member.

13. The tissue cutting device according to claim 11 or 12, further comprising a pouch extending from a front end portion inserted into a patient's body to a base end portion left outside the patient's body,
   wherein an opening portion into which a tissue can be inserted is formed in a side portion from the front end portion to the base end portion.

14. The tissue cutting device according to claim 13, wherein the pouch has an opening in a proximal side and a slit extending from the opening to the opening portion is provided.

15. The tissue cutting device according to claim 13, wherein a member arranging the top portions of the loop portions is attached to the pouch so that the top portions of the loop portions are arranged in the first arrangement along the opening portion of the pouch.

16. The tissue cutting device according to claim 15, wherein the pouch does not have an opening in a front end side relative to the opening portion and the opening portion can be extended outside a patient's body while the tissue before shredding is housed in the pouch.

17. The tissue cutting device according to claim 16, wherein a cross-sectional area of a front end portion of the pouch is smaller than a cross-sectional area of a tissue to be shredded.

18. The tissue cutting device according to claim 17, further comprising an opening support section attached to the opening portion of the pouch, which holds a shape of the opening portion,
   wherein a break section capable of cutting off the pouch from the opening support section is provided in a periphery of the opening portion.

19. The tissue cutting device according to claim 10, wherein the loop portions extended from the shredding pipe in the second arrangement are longer in a center part than in a front end and a base end.

20. The tissue cutting device according to claim 19, wherein the arrangement of the loop portions is held while the second arrangement is switched over to the third arrangement.

* * * * *